US012465772B2

(12) United States Patent
Perryman et al.

(10) Patent No.: US 12,465,772 B2
(45) **Date of Patent: *Nov. 11, 2025**

(54) RELAY MODULE FOR IMPLANT

(71) Applicant: Curonix LLC, Pompano Beach, FL (US)

(72) Inventors: Laura Tyler Perryman, Pompano Beach, FL (US); Chad Andresen, Miami Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/238,700

(22) Filed: Aug. 28, 2023

(65) Prior Publication Data

US 2023/0405341 A1 Dec. 21, 2023

Related U.S. Application Data

(63) Continuation of application No. 17/193,191, filed on Mar. 5, 2021, now Pat. No. 11,745,020, which is a continuation of application No. 15/983,355, filed on May 18, 2018, now abandoned, which is a continuation of application No. 15/002,610, filed on Jan. 21, 2016, now Pat. No. 9,974,965, which is a continuation of application No. 13/621,530, filed on Sep. 17, 2012, now Pat. No. 9,242,103.

(60) Provisional application No. 61/535,295, filed on Sep. 15, 2011.

(51) Int. Cl.
*A61N 1/372* (2006.01)
*A61N 1/36* (2006.01)
*A61N 1/378* (2006.01)

(52) U.S. Cl.
CPC ..... *A61N 1/37229* (2013.01); *A61N 1/36125* (2013.01); *A61N 1/37223* (2013.01); *A61N 1/3787* (2013.01)

(58) Field of Classification Search
CPC ... A61N 1/3787; A61N 1/3722; A61N 1/3612
See application file for complete search history.

(56) References Cited

U.S. PATENT DOCUMENTS 9,242,103 B2 * 1/2016 Perryman .......... A61N 1/36125

* cited by examiner

*Primary Examiner* — Alyssa M Alter
(74) *Attorney, Agent, or Firm* — Maschoff Brennan

(57) ABSTRACT

An implementation provides a system that includes: a control module including a first antenna, the control module configured to generate a first radio frequency (RF) signal and transmit the first RF signal using the first antenna; an implantable lead module including a second antenna and at least one electrode configured to stimulate excitable tissue of a subject; and a relay module configured to receive the first RF signal; generate a second RF signal based on the first RF signal, the second RF signal encoding a stimulus waveform to be applied by the at least one electrodes of the implantable lead module to stimulate the excitable tissue of the subject; and transmit the second RF signal to the implantable lead module.

20 Claims, 34 Drawing Sheets

Antenna with Circuitry Between Antennas Profile View

Antenna with Circuitry on Top Profile View

RELAY MODULE FOR IMPLANT

CROSS REFERENCE TO RELATED APPLICATIONS

This application is a continuation of U.S. application Ser. No. 17/193,191, filed Mar. 5, 2021, which is a continuation of U.S. application Ser. No. 15/983,355, filed May 18, 2018, now abandoned, which is a continuation of U.S. application Ser. No. 15/002,610, filed Jan. 21, 2016, now U.S. Pat. No. 9,974,965, issued May 22, 2018, which is a continuation of U.S. application Ser. No. 13/621,530, filed Sep. 17, 2012, now U.S. Pat. No. 9,242,103, issued Jan. 26, 2016, which claims the benefit of U.S. Provisional Application No. 61/535,295, filed Sep. 15, 2011, the entire contents of which are hereby incorporated by reference.

BACKGROUND

Active implanted stimulation devices have been utilized for applications such as pacing, defibrillation, spinal and gastric stimulation. Such devices typically include wired electrodes on a lead module hardwired to an implanted pulse generator (IPG) that contains an internal battery that can be recharged periodically with an inductive coil recharging system.

SUMMARY

In one aspect, a system includes a control module including a first antenna, the control module being configured to generate a first radio frequency (RF) signal and transmit the first RF signal using the first antenna; an implantable lead module including a second antenna and at least one electrode configured to stimulate excitable tissue of a subject; and a relay module configured to: receive the first RF signal; generate a second RF signal based on the first RF signal with the second RF signal encoding a stimulus waveform to be applied to the electrodes of the implantable lead module to stimulate excitable tissue of a subject; and transmit the second RF signal, wherein the implantable lead module is configured to receive the second RF signal using the second antenna, generate the stimulus waveform from the received second RF signal, and apply the stimulus waveform to the excitable tissue of the subject.

Implementations of this and other aspects may include the following features: a control module which may include a programming interface to allow a user to adjust parameters of the stimulation waveform; a first antenna of the control module which may include a dipole antenna, a folded dipole antenna, a microstrip antenna, or a phased array of antennas.

The relay module may include: a receive antenna layer configured to receive the first RF signal transmitted by the first antenna of the control module; at least one dielectric insulating layer; and a transmit antenna layer separated from the receive antenna layer by the dielectric insulating layer, the transmit antenna layer being configured to transmit the second RF signal to the second antenna of the implantable lead module, the second RF signal being generated based on the first RF signal, and the second RF signal encoding a stimulus waveform to be applied by the at least one electrode of the implantable lead module to stimulate the excitable tissue of the subject.

The receive antenna layer of the relay module may include one of: a patch antenna, or a dipole antenna. The receive antenna layer may further include at least one quarter wavelength antenna. The transmit antenna layer of the relay module may include one of: a patch antenna, or a dipole antenna. The transmit antenna layer may further include at least one quarter wavelength antenna.

The relay module may further include a flexible circuit, wherein the flexible circuit may include a rectifier and a capacitor, and wherein the capacitor is coupled to the rectifier and configured to store a charge during an initial portion of the first RF signal. The flexible circuit may further include a counter configured to cause the flexible circuit to generate a trigger upon an end of the initial portion. The flexible circuit may further include an oscillator, coupled to the counter and configured to generate, upon the trigger, a carrier signal, and wherein the flexible circuit may modulate the carrier signal with a stimulus waveform encoded in the first RF signal to generate the second RF signal. The flexible circuit may be configured to generate the second RF signal based on the stimulus waveform during a stimulation portion of the first RF signal, wherein the second RF signal has a corresponding carrier frequency that is substantially identical to that of the first RF signal. The flexible circuit may further include a power amplifier configured to amplify the second RF signal, and wherein the transmit antenna layer may be configured to transmit the amplified second RF signal to the second antenna of the implantable lead module. The power amplifier may be powered by the charge stored in the capacitor during the initial portion of the first RF signal. The oscillator may be triggered by an amplitude shift keying in the first RF signal.

The first RF signal and the second RF signal may have respective carrier frequencies that may be within a range of about 800 MHz to about 6 GHz. The respective carrier frequencies of the first and second RF signals may be different.

The relay module may be placed exterior to the subject and the relay module may further include a battery. The relay module may be subcutaneously placed underneath the subject's skin. The relay module may be placed on the subject's skin. The relay module is placed on a wearable item.

The relay module may further include a position sensor configured to read positional information of the relay module. The position sensor comprises one of: a touch sensor, a gyroscope, or an accelerometer. The control module may be further configured to: receive the positional information from multiple relay modules; and choose a particular relay module to transmit the second RF signal to the implantable lead module, based on the positional information received, wherein the particular relay module chosen is better coupled to the implantable lead module than at least one other relay module.

In another aspect, a method of stimulating excitable tissue in a subject by using a relay module includes: transmitting a first RF signal from a first antenna on a control module; receiving, by the relay module, the first RF signal from the first antenna on the control module; generating, by the relay module, a second RF signal based on the first RF signal, the second RF signal containing power and encoding a stimulus waveform to be applied by the at least one electrodes of the implantable lead module to stimulate excitable tissue of the subject; transmitting, by the relay module, the second RF signal to an implantable lead module; receiving, by the implantable lead module the second RF signal; generating, by the implantable lead module the stimulation waveform; and applying, through at least one electrode on the implantable lead module, the stimulation waveform to the excitable tissue.

Implementations of this and other aspects may further include rectifying an initial portion of the first RF signal to provide energy to store a charge on the relay module; generating the second RF signal at an end of the initial portion; and amplifying the second RF signal by using the stored charge before transmitting the second RF signal.

The method may further include: generating the second RF signal based on a trigger caused by an amplitude shift keying in the first RF signal, the amplitude shift keying corresponding to the end of the initial portion of the first RF signal. The method may further include: generating the second RF signal based on a trigger caused by counting a number of cycles during the initial portion of the first RF signal.

The second RF pulse may include a portion to provide energy to power the implantable lead module. The method may further include: configuring polarity of at least one electrode of the implantable lead module based on a subsequent portion of the second RF signal that encodes polarity setting information of the at least one electrode.

The details of one or more implementations are set forth in the accompanying drawings and the description below. Other features, objects, and advantages will be apparent from the description and drawings, and from the claims.

DETAILED DESCRIPTION

Figure 1:
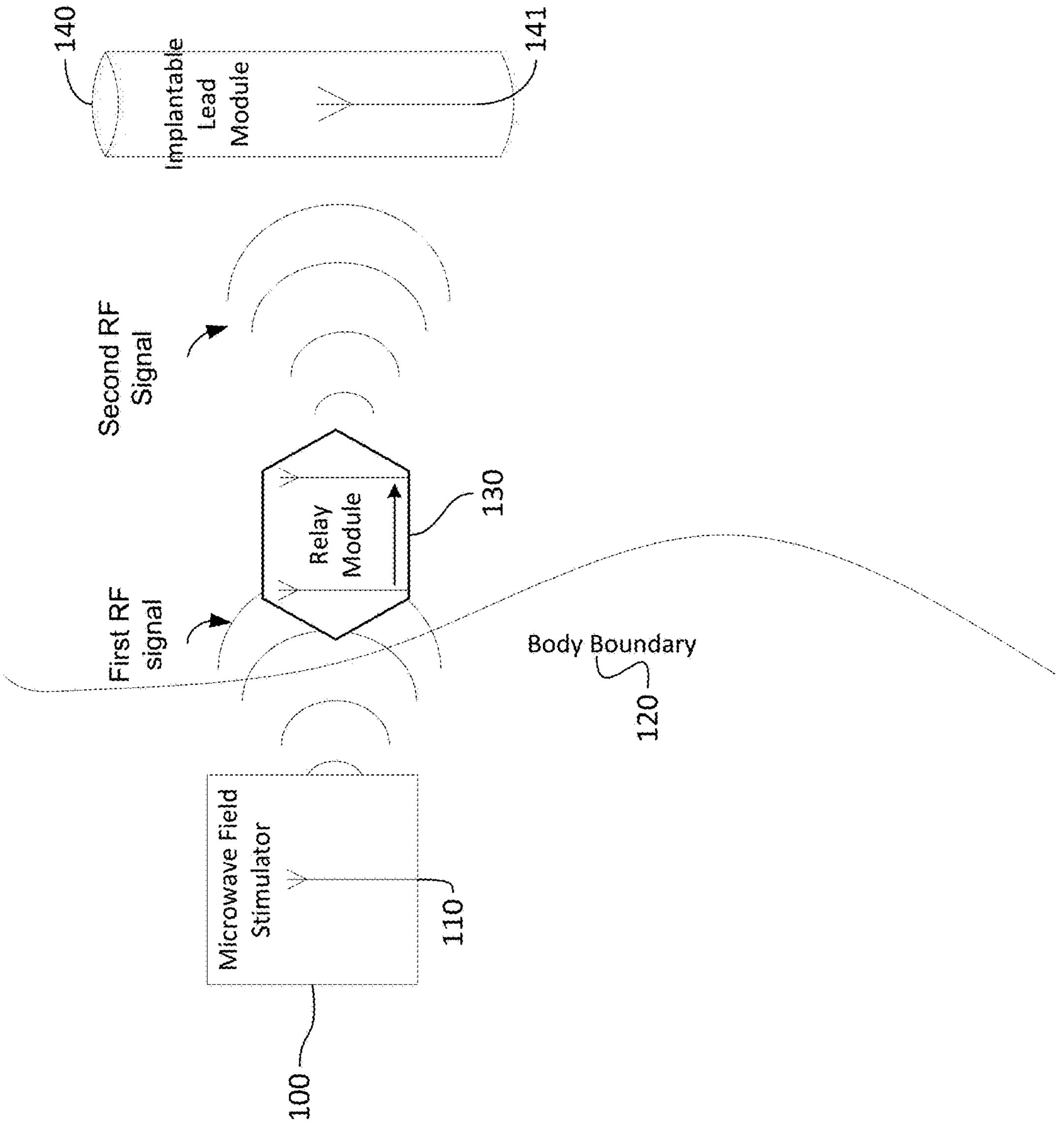
FIG. 1 shows an example of a wireless stimulation system including a relay module.

FIG. 1 shows an example of a wireless stimulation system including a relay module 130. The wireless stimulation system includes a control module, such as a portable microwave field simulator (MFS) device 100, the relay module 130, and an implantable lead module 140, which may be an implantable neural stimulator. In the example shown in FIG. 1, the lead module 140 is implanted in a subject, such as a human patient, or an animal.

The portable MFS device 100 includes an antenna 110. Antenna 110 may be configured to transmit a first radio frequency (RF) signal that propagates to relay module 130. The first RF signal may have a characteristic carrier frequency within a range from about 800 MHz to about 6 GHz.

As shown by FIG. 1, the relay module 130 may be placed subcutaneously under the skin of a subject. The first RF signal from antenna 110 may propagate through body boundary 120 to reach relay module 130. Relay module 130 may also be placed outside body boundary, for example, on the patent's skin topically. Relay module 130 may also be placed as a wearable item, as will be discussed in further detail later.

Relay module 130 may include a receive antenna 131 and a transmit antenna 132. Receive (Rx) antenna 131 is configured to receive the RF signal from antenna 110. The coupling between antenna 110 and Rx antenna 131 may be inductive, radiative, or any combinations thereof. The Rx antenna 131 may be coupled to transmit (Tx) antenna 132 by a dielectric insulating layer(s) and flexible circuits, as will be discussed in further detail below. The Tx antenna 132 transmits a second RF signal to an implantable lead module 140. The second RF signal may be derived from, or otherwise based on, the first RF signal and may or may not have the same characteristic carrier frequency of the first RF signal, as will be discussed in further detail below. A RF module 130 may use, for example, a conditioning circuit in combination with a power amplifier to shape and enhance the second RF signal before transmitting the second RF signal to implantable lead module 140, as will be discussed below in further detail.

An implantable lead module 140 has been implanted inside the body of a subject. The subject can be a live human or animal. The implantable lead module 140 is a passive device without an onboard power source, such as a battery. An implantable lead module 140 includes an antenna 141 configured to receive the second RF signal from antenna 132. The coupling between antenna 141 and Tx antenna 132 may be inductive, radiative, or any combinations thereof. The implantable lead module 140 includes one or more electrodes placed in close proximity to an excitable tissue, such as, for example, neural tissue. The second RF signal may contain energy to power the lead module 140, and may encode a stimulus waveform. The lead module 140 may generate the stimulus waveform from the second RF signal, and apply the stimulus waveform to the excitable tissue using the electrodes. Examples of the lead module 140 are described in, for example, U.S. patent application Ser. No. 13/584,618, filed on Aug. 13, 2012, the entire contents of which are incorporated herein by reference.

Figure 2A:
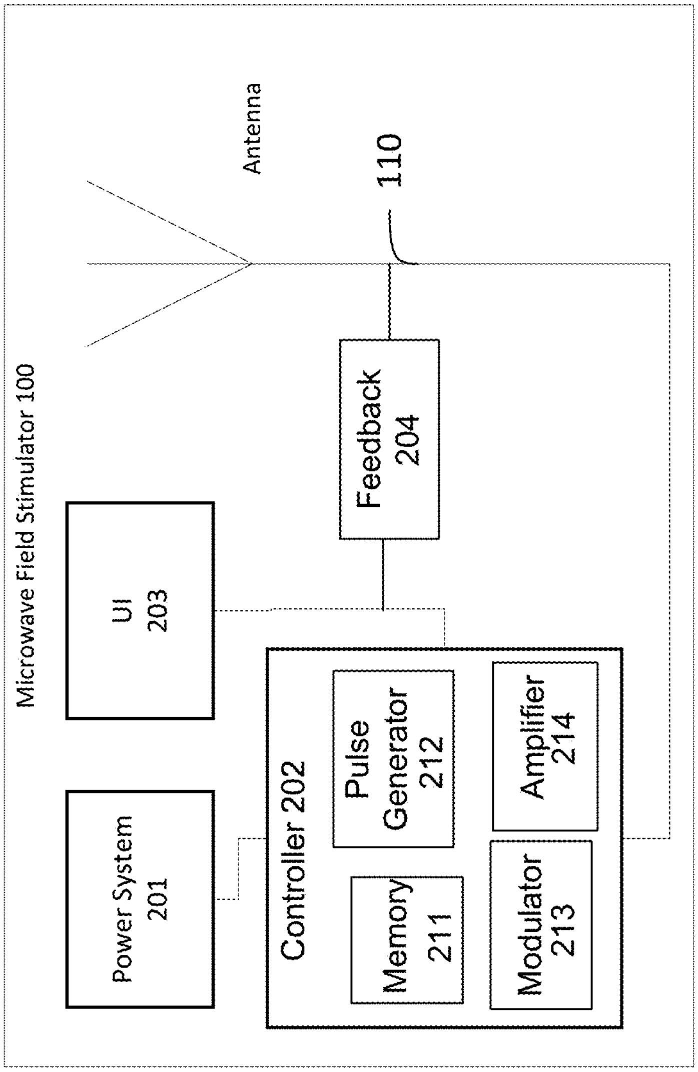
FIGS. 2A and 2B show example of a portable Microwave Field Stimulator (MFS) device.
Figure 2B:
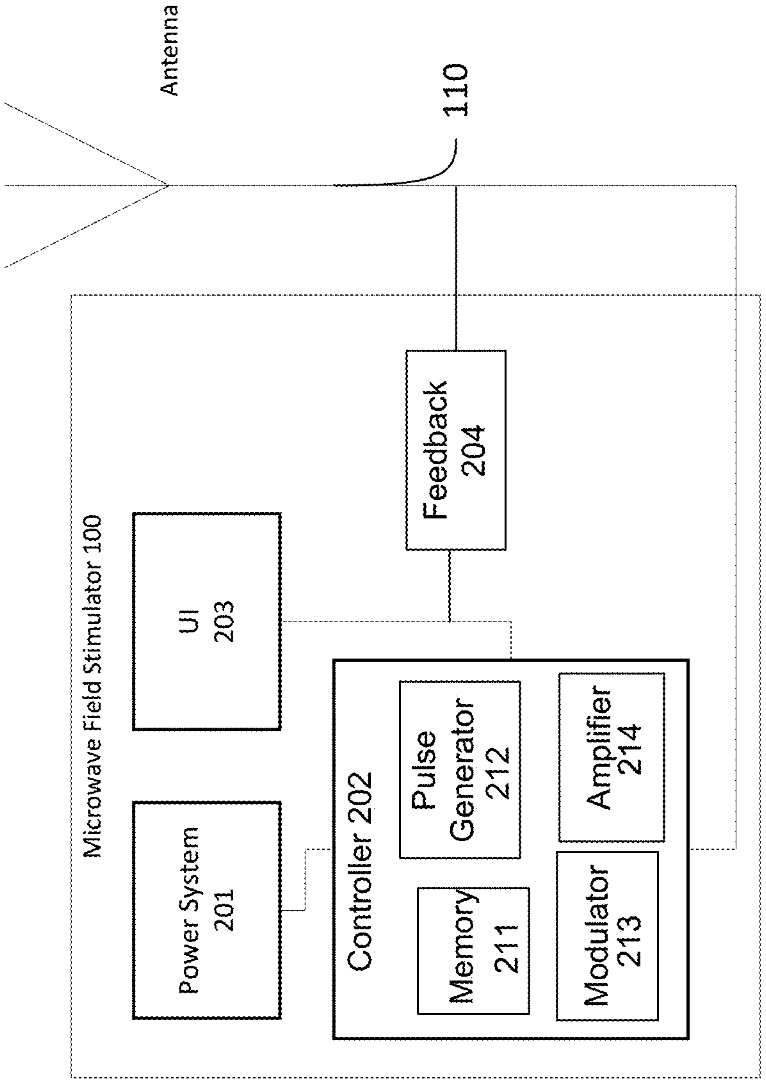

FIGS. 2A and 2B show examples of a portable Microwave Field Stimulator (MFS) device. A portable MFS device 100 may include a power system 201, a controller 202, a user interface (UI) 203, a feedback subsystem 204, and antenna 110. Examples of the MFS are described in, for example, U.S. patent application Ser. No. 13/584,618, filed on Aug. 13, 2012.

As illustrated by FIG. 2A, a power system 201 may include a battery, for example, a rechargeable power source such as, for example, a lithium-ion battery, a lithium polymer battery, etc. The power system 201 provides power to a portable MFS device 100.

The controller 202 can create the first RF signal to be transmitted from the antenna 110 to the relay module 130, which in turn may generate and transmit the second RF signal to the antenna 141 on the implantable lead module 140. As shown in FIG. 2A, the controller 202 may include memory 211, pulse generator 212, modulator 213, and amplifier 214.

Memory 211 may be local memory on board of the portable MFS device 100. Memory 211 may include any type of non-volatile memories, such as, for example, EEPROM, flash memory, etc. Memory 211 may store stimulation parameter settings, such as for example, pulse amplitude, waveform shape, repetition frequency, pulse duration, etc. Based on the stored stimulation parameter settings, pulse generator 212 may generate stimulation waveforms. Modulator 213 may generate a carrier frequency, for example, within a range from about 600 MHz to about 6 GHz. The stimulation waveforms generated by pulse generator 212 may modulate the carrier frequency. The resulting modulated carrier frequency signal may be amplified by amplifier 214 to generate the first RF signal to be transmitted by antenna 110.

The controller 202 may receive input from the UI 203 and the feedback subsystem 204. UI 203 may include a Bluetooth circuit board, or a USB interface connector. UI 203 may include a programmer interface for a user, such as a manufacturer's representative, to adjust stimulation parameters, such as, for example, stimulation frequency, pulse width, power amplitude, duration of treatment, waveform shape, pre-programmed options and patient reminders. The programming interface can cause the selected settings to be stored on memory 211 of controller 202. The selected settings are used to create, for example, the appropriate stimulation waveforms for driving the electrodes on implantable lead module 140.

Feedback subsystem 204 also may provide input to the controller 202 in creating the first RF signal. The feedback may be based on measurements of reflected power on antenna 110. The reflected power may indicate the coupling between antenna 110 and surrounding medium, as will be discussed in further detail in association with FIG. 10.

Antenna 110 may include a dipole antenna, a folded dipole antenna, a patch antenna, a microstrip antenna, or a phased array of antennas. Antenna 110 may be impedance matched to air to improve coupling efficiency with relay module 130. Antenna 110 can be located on the top of a flexible fixation housing that encloses the MFS circuitry connected with a low loss cable, or within the MFS enclosure, or remote from the MFS connected through a low loss cable.

FIG. 2A illustrates an implementation in which the antenna 110 is housed within the enclosure of the portable MFS device 100. The housing enclosure of portable MFS device 100 can be made of materials such as neoprene, or polyurethane, or other similar material with similar dielectric properties.

In another example, shown in FIG. 2B, antenna 110 may be located on the outside of the portable MFS device 100 within a separate encasement by which the MFS power is hardwired to the antenna by a low loss cable. The antenna 110 can be located as far as three feet from the relay module 130, or alternatively may be coupled directly to the skin in the proximity of the implanted lead module 140.

Figure 3:
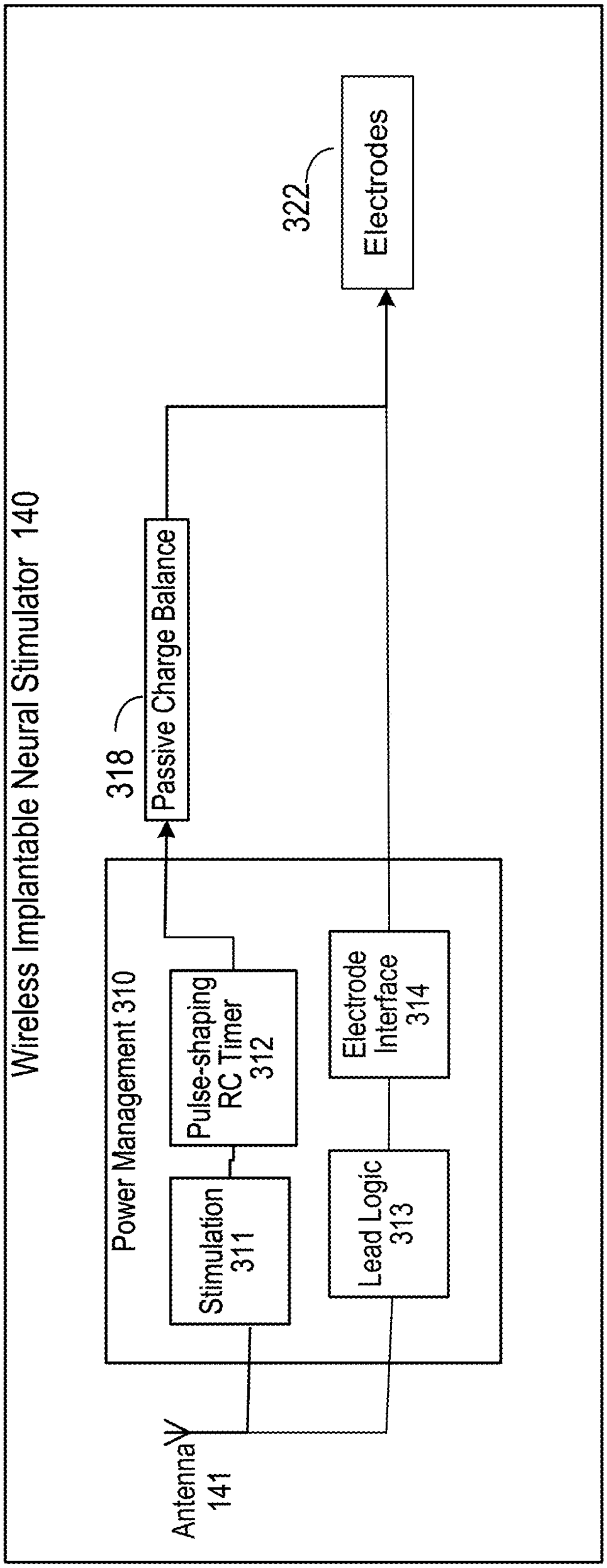
FIG. 3 is a block diagram showing an example of implantable lead module.

FIG. 3 is a block diagram showing an example of implantable lead module 140. Implantable lead module 140 is a passive device without an active power supply, such as a battery. Implantable lead module 140 may be an implantable neural stimulator. Implantable lead module 140 may include antenna 141, power management circuitry 310, passive charge balance circuitry 318, and electrodes 322.

Antenna 141 is configured to receive the second RF signal from antenna 132 on relay module 130. The Antenna 141 may be embedded as a dipole, a patch, a microstrip, folded dipole, other antenna configuration. The second RF signal may have a carrier frequency in the GHz range and contain electrical energy for powering the wireless implantable lead module 140 and for providing stimulation pulses to electrodes of implantable lead module. Once received by the antenna 141, the second RF signal is routed to power management circuitry 310 as the input signal.

Power management circuitry 310 is configured to rectify the input signal and convert it to a DC power source. For example, the power management circuitry 310 may include a diode rectification bridge and a capacitor. The rectification may utilize one or more full wave diode bridge rectifiers within the power management circuitry 310.

The DC power source provides power to the stimulation circuitry 311 and lead logic circuitry 313. Stimulation circuitry 311 may extract the stimulation waveforms from the received input signal. The stimulation waveforms may be shaped by pulse shaping RC timer circuitry 312 and then applied to the electrodes 322. Passive charge balancing circuitry 318 may balance charges applied at the electrodes. Lead logic circuitry 313 may detect a portion of the input signal containing polarity setting information for each electrode of the electrode array 322. This information may be used to set the polarity of electrode interface 314 controlling the polarity assignment of each electrode on electrodes 322. A particular electrode on the electrode array 322 may be implanted near target excitable tissue. The excitable tissue can be, for example, a cardiac tissue, a neural tissue, etc.

Figures 4A, 4B, 4C:
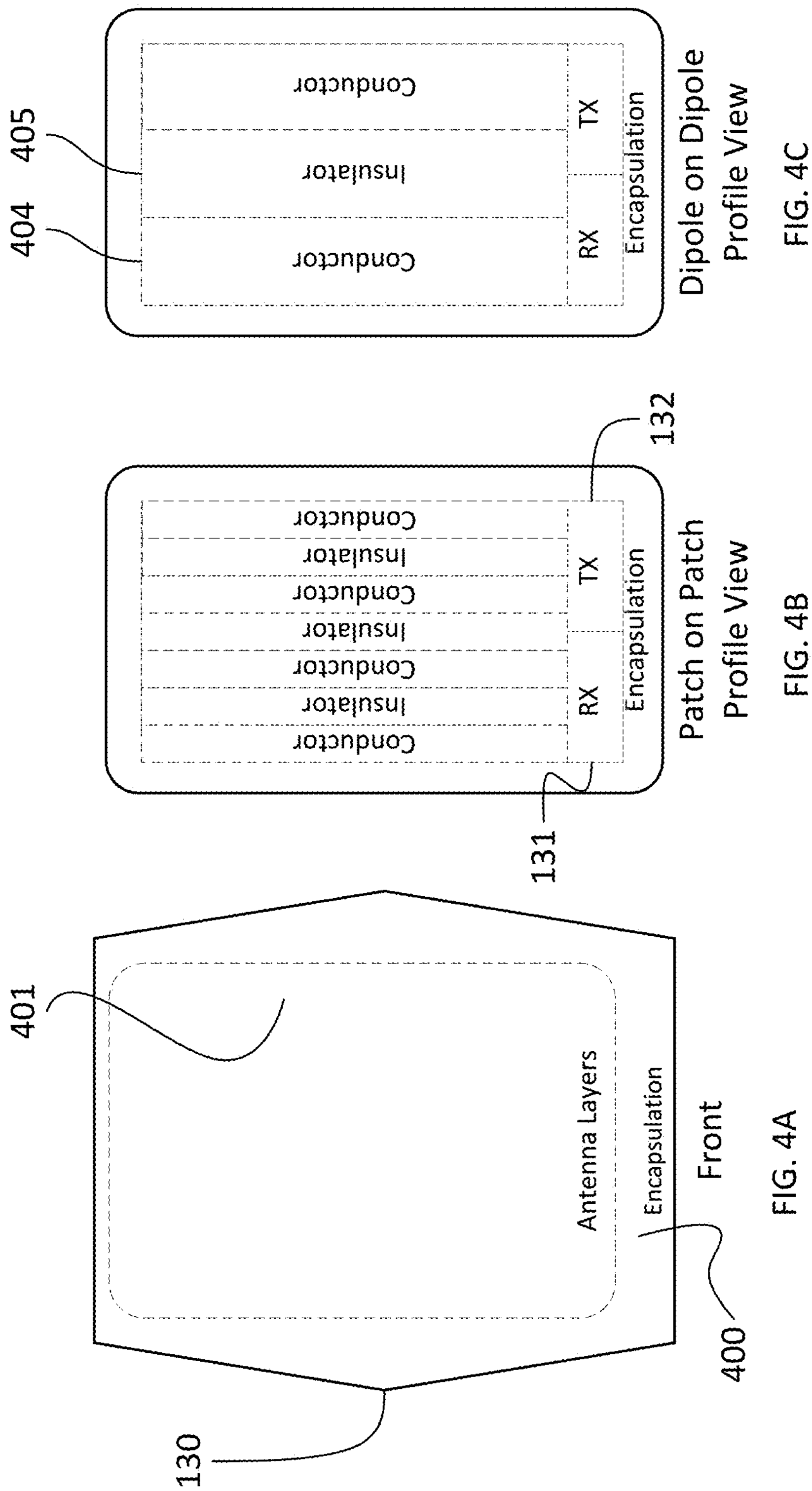
FIGS. 4A-4C show examples of configurations of a relay module.

FIGS. 4A-4C show examples of configurations of a relay module 130. A relay module 130 may include encapsulation materials 400 and antenna layers 401, as shown by FIG. 4A. Encapsulation materials 400 may be any material that encapsulates relay module 130, such as most plastics. The antenna layers 401 may be encapsulated underneath encapsulation material 400.

FIG. 4B shows a profile view of one example of a layered configuration for the Rx antenna 131 and the Tx antenna 132. Rx 131 in FIG. 4B is a patch antenna formed by a layered structure of two conductor layers 404 and one insulator layer 405 in between. The conductor layers 404 may include any appropriate conducting metal, for example, copper, silver, etc. The insulator layer 405 may include insulating dielectric materials, such as, for example, porcelain, glass, and most plastics.

As discussed above, relay module 130 may be placed either in proximity of the tissue medium within a few millimeters or subcutaneously under the skin of a subject, such as a human or an animal. If placed outside the subject's body, the Rx antenna 131 may be coupled to the air and may be impedance-matched to the air. If placed subcutaneously, the Rx antenna 131 may still be coupled to the air since the skin layer covering the antenna is sufficiently thin, having minimal effect on the coupling efficiency between the antenna 110 and Rx antenna 131 of the relay module 130. The separation of the two conductor layers 404 and the electromagnetic properties of the insulator layer 405 may determine the resonant frequency of Rx antenna 131. Rx antenna 131 may generally be a quarter wavelength antenna at this resonant frequency.

The Tx antenna 132 in FIG. 4B is also a patch antenna formed by a layered structure of two conductor layers 404 and one insulator layer 405 in between. Likewise, the separation of the two conductor layers 404 and the electromagnetic properties of the insulator layer 405 may determine the resonant frequency of Tx antenna 132. Similarly, Tx antenna 131 may also be a quarter wavelength antenna at this resonant frequency. In contrast to the Rx antenna 131, which may be coupled to the air, Tx antenna 132 may be coupled to the tissue, especially when relay module 130 is placed subcutaneously. Tx antenna 132 may then be impedance matched to tissue to improve coupling efficiency when transmitting the second RF signal to implantable lead module 140 inside the subject's body. The transmitting metal layer may have a smaller surface area than the ground plane and may have a specific shape for improved coupling with surrounding tissue (e.g., if placed topically on the subject's skin). As illustrated, Tx antenna 132 in FIG. 4B is separated by another insulator layer 405 from Rx antenna 131.

Generally, a patch antenna may include a conducting material layer that serves as a conducting plane; a dielectric insulating plane the size of the conducting plane placed over the conducting layer; and another conducting layer, smaller than the ground plane, shaped in a desired pattern. If two patch antennas are separated by another insulating plane, as illustrated by FIG. 4B, the E-field of the transmit patch antenna does not interact with the E-field of the receive patch antenna on the other side of the relay module, when no edge-effects are present.

FIG. 4C shows a profile view of another configuration of Rx antenna 131 and Tx antenna 132 configured as dipole antennas. In this configuration, the Rx antenna 131 is formed by the shape and contour of the surface of one conductor layer 404 while the Tx antenna 132 is formed by the shape and contour of another conductor layer 404. The two conductor layers are separated by an insulator layer 405. The shape and contour of each conductor layer may generally determine the corresponding resonant frequency. In this configuration, the Rx antenna 131 and the Tx antenna may also be quarter-wavelength antennas at their respective resonant frequencies.

In FIGS. 4B and 4C, the ground plane of the Tx antenna 132 may face away from the active radiator of the antenna 110 and the transmitting surface of Tx antenna 132 may face towards tissue in order to improve the efficiency of the Tx antenna 132 in relaying energy to the antenna 141 on implantable module 140. Additionally, Rx antenna 132 may have a surface area much larger than antenna 141 on the implantable module 140. For example, in certain embodiments, the Rx antenna 132 may have surface area of four square centimeters or above, while the antenna 141 within the implanted lead module may have a surface area less than one tenth of a square centimeter. The Rx antenna 131 may thus capture a much larger portion of the flux of EM energy (for example, hundreds of times larger) and relay that energy to the antenna 141 through the relay module Tx antenna 132. Although FIGS. 4B and 4C respectively show a patch-on-patch configuration and a dipole-on-dipole configuration, other arrangements may be implemented, such as, for example, a patch-on-dipole or a dipole-on-patch configuration.

Figure 5C:
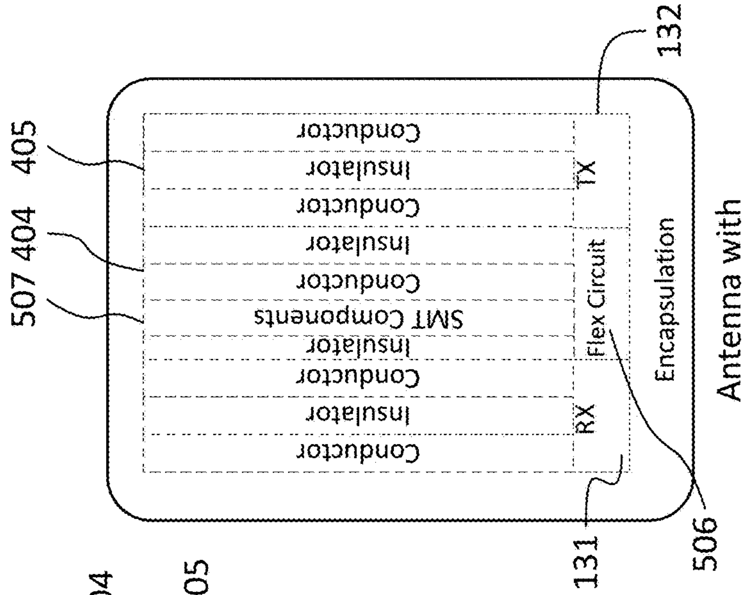
FIGS. 5A-5C show examples of configurations of a relay module with a flexible circuit.
Figure 5B:
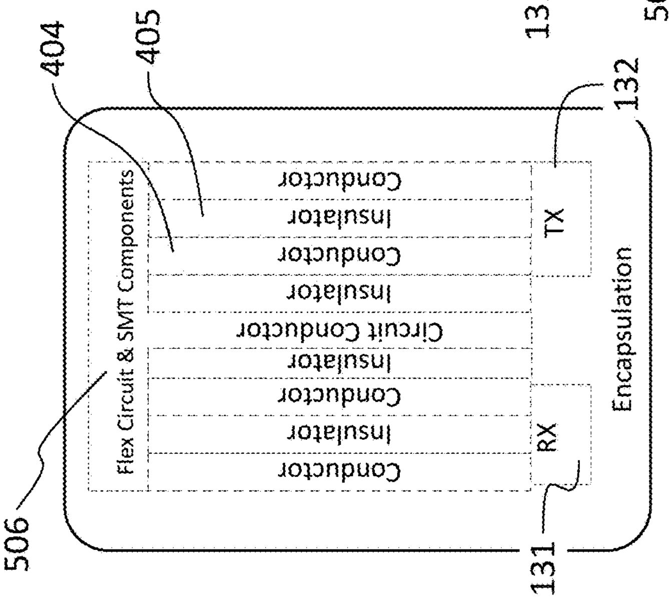
Figure 5A:
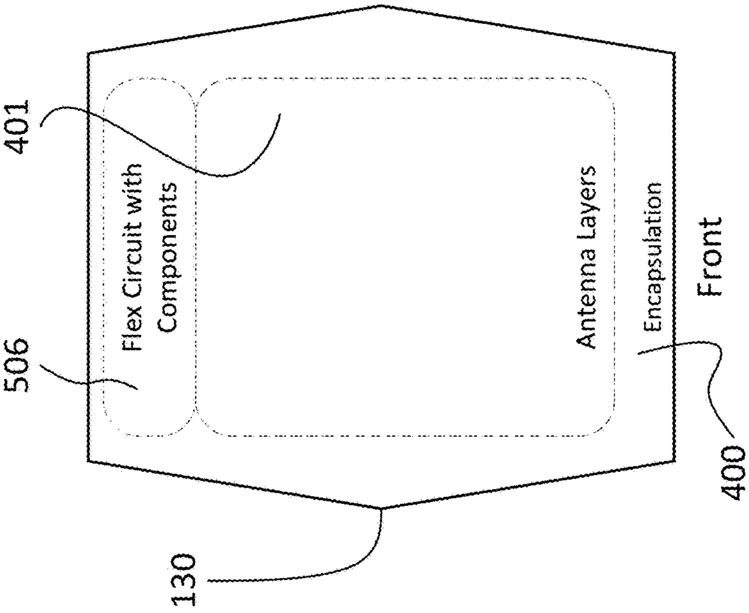

FIGS. 5A-5C show examples of configurations of a relay module 130 with a flexible circuit. The RF signal may be received by a Rx antenna 131 from the antenna 110. This received RF signal may be modulated and amplified via circuitry on a flexible circuit within the relay module 130. The flexible circuit may be implemented in a flexible circuit board substrate that is easily bendable within the body or on the surface of the skin. These electronics may be isolated from the antenna ground planes by a layer of insulation. A layer of conductive material may provide the interconnections to route the input signal from the Rx antenna 131 and send the conditioned and amplified signal out through the Tx antenna 132. This circuitry may include amplification and conditioning functions, as will be discussed in detail in association with FIGS. 6-8.

The flexible circuit may be placed relative to the Rx antenna 131 and the Tx antenna 132. For example, FIGS. 5A and 5B respectively show the front view and the profile view of a configuration in which the flex circuit 506, along with the components, are placed on the side of the antenna layers. In another example, FIG. 5C shows the profile view of another configuration in which the flexible circuit 506 and the surface mount (SMT) flexible circuit components 507 are placed in between the antenna layers. Additionally, although not shown, the flexible circuit may also be placed on the top or bottom of the antenna layers.

The relay module 130 may operate in two modes, a relay mode and a repeater mode. In relay mode, the relay module 130 may not alter the stimulation portion of the received first RF signal when transmitting the second RF signal to the implantable lead module 140. In the repeater mode, however, the relay module 130 may enhance the stimulation portion of the received first RF signal when transmitting the second RF signal to the implantable lead module 140.

Figure 6:
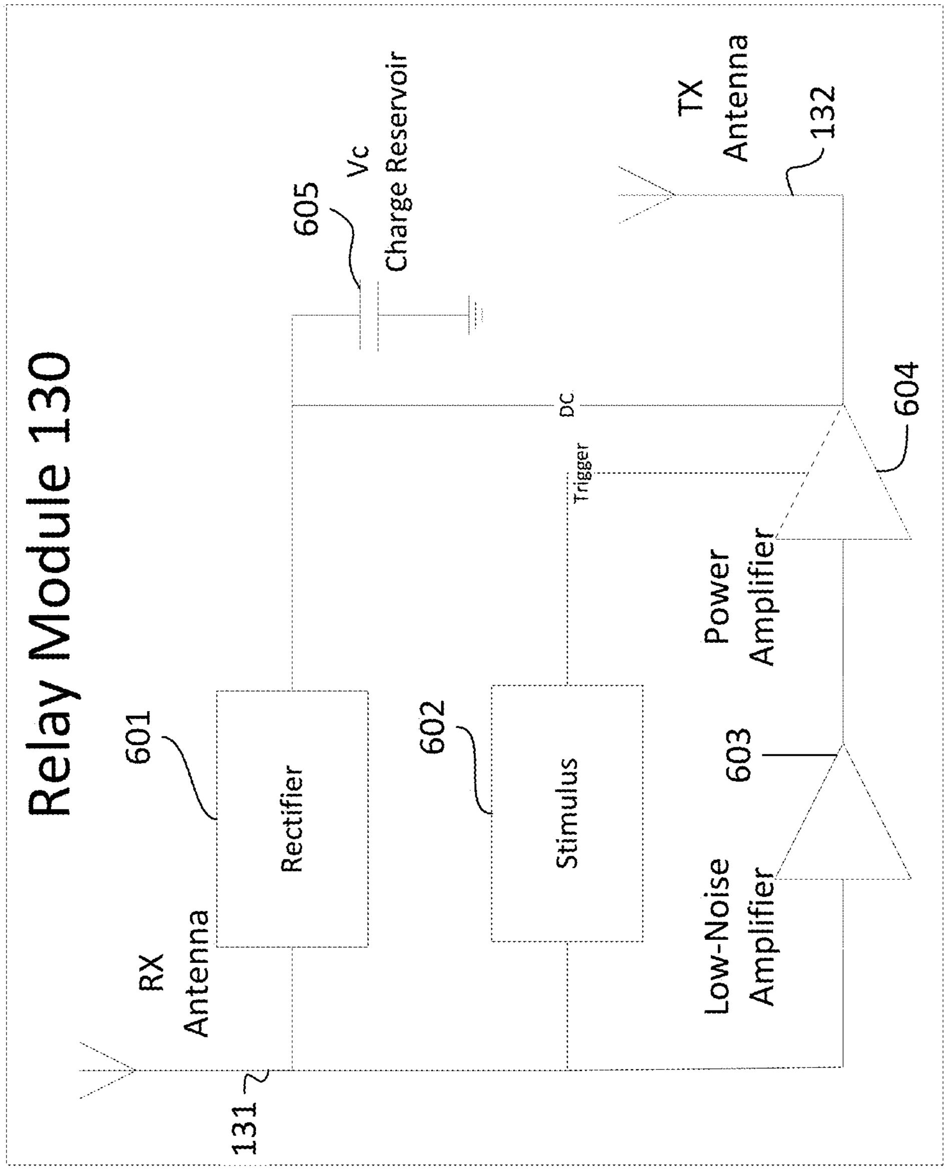
FIG. 6 is a block diagram showing an example of a circuit, such as a flexible circuit, used on a relay module.

FIG. 6 is a block diagram showing an example of a circuit, such as a flexible circuit, used on the relay module 130. In this mode, relay module 130 operates as an RF signal replicator to transmit the second RF signal at the same carrier frequency as the stimulus portion of the received first RF signal from the portable MFS device 100.

The first RF signal transmitted from the portable MFS device 100 contains two separate portions of encoded carrier waveforms. The first RF signal is received by Rx antenna 131 on relay module 130. A charging portion of the received first RF signal may contain a long (e.g., about 1 ms or above) burst of pulses at a carrier frequency. This charging portion may be the initial portion of a particular signal pattern to be repeated in the first RF signal. This charging portion is used to charge a power storage reservoir circuit including a capacitor 605 within the relay module 130. For example, the flexible circuit may contain a rectifier 601 to generate a DC power supply by rectifying and smoothing the initial portion of the received first RF signal. The DC power supply may store charges in, for example, capacitor 605. The stored charge may then be used to power subsequent operations of relay module 130. These subsequent operations may include, for example, subsequent transmission of the second RF signal that powers the electrodes on implantable lead module 140. Specifically, implantable lead module 140 is a passive device without a power supply. In contrast, some implementations of the relay module 130, however, may include a power source, such as a rechargeable battery. Once the second RF signal is received at the passive implantable lead module 140, it may be demodulated to provide the stimulation waveforms to be applied at the electrodes 322. As discussed above in association with FIG. 3, in some implementations, the second RF signal may also contain polarity setting information to be applied in assigning the polarity of each electrode of the electrode array 322. Details are discussed in U.S. patent application Ser. No. 13/584,618, filed on Aug. 13, 2012. Thus, by transmitting the second RF signal, derived from or otherwise based on the first RF signal transmitted from portable MFS device 100, relay module 130 of FIG. 6 can power a passive lead module 140.

A stimulation portion of the received first RF signal encodes stimulus waveforms. This stimulation portion may be the later portion of the signal pattern being repeated in the first RF signal. The stimulation portion of the first RF signal will be conditioned by stimulus conditioning circuitry 602 before transmission to implantable lead module 140. The stimulus waveforms may contain short (e.g., about 0.5 ms or shorter) bursts of pulses. A low-noise amplifier 603 detects the stimulation portion of the first RF signal from Rx antenna 131 and feeds the stimulation portion to a high power amplifier 604. In one implementation, the first RF signal contains amplitude shift keying to indicate the end of the initial portion (for charging, e.g., capacitor 605) and the start of the stimulation portion. The amplitude shift keying may cause the stimulus conditioning circuitry 602 to generate a trigger to allow DC power to be received from the stored charge in capacitor 605. In another implementation, the stimulus conditioning circuit may include a counter that is set to expire upon a pre-determined number of pulse wave cycles. When the counter counts the number of pulse cycles in the received first RF signal has reached the pre-determined threshold, the counter will expire and generate a trigger. Upon the trigger, stored charge in capacitor 605 may be harvested to power, for example, stimulus conditioning circuit 602, low-noise amplifier 603 and power amplifier 604. In either example implementation, the output from the power amplifier 604 drives the Tx antenna 132 to transmit the amplified stimulus waveform at the original carrier frequency to the implantable lead module 140. The stored charge can be recharged by the next repetition of the initial portion in the first RF signal received from portable MFS device 100.

Figure 7:
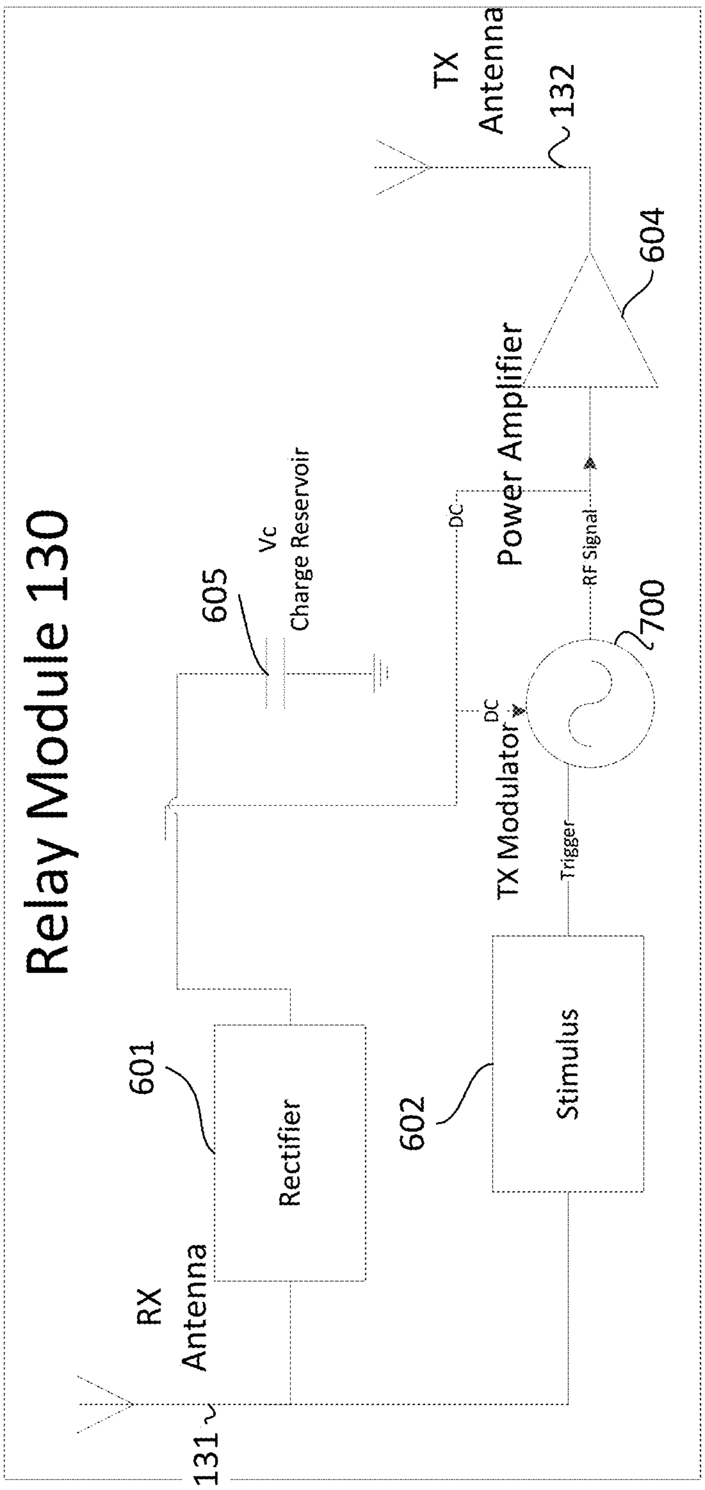
FIG. 7 is a block diagram showing another example of a circuit, such as a flexible circuit, used on the relay module.

FIG. 7 is a block diagram showing another example of a circuit, such as a flexible circuit, used on the relay module 130. In this mode, relay module 130 acts as an active modulated pulse transmitter. The modulator 600 can provide a carrier signal at a different frequency than the frequency of the first RF signal received from the portable MFS device 100. The first RF signal is received by the Rx antenna 131 coupled to air.

The first RF signal received from portable MFS device 100 by Rx antenna 131 contains two separate portions of encoded carrier waveforms. As discussed above, an initial portion of the first RF signal may contain a long (e.g., about 1 ms or above) burst of pulses at a carrier frequency. This initial portion is used to charge a power storage reservoir circuit including a capacitor 605 within the relay module 130. For example, the flexible circuit may contain a rectifier 601 to generate a DC power supply by rectifying and smoothing the initial portion of the first RF signal. The DC power supply may store charges in, for example, capacitor 605. The stored charge may then be used to power subsequent power subsequent operations of relay module 130. These subsequent operations may include, for example, subsequent transmission of the second RF signal that powers the electrodes on implantable lead module 140. As discussed above, implantable lead module 140 is a passive device without a power supply. In contrast, some implementations of the relay module 130, however, may include a power source, such as a rechargeable battery. Once the second RF signal is received at the passive implantable lead module 140, it may be demodulated to provide the stimulation waveforms to be applied at the electrodes 322. As discussed above in association with FIG. 3, in some implementations, the second RF signal may also contain polarity setting information to be applied in assigning the polarity of each electrode of electrodes 322. Details of discussed in U.S. patent application Ser. No. 13/584,618, filed on Aug. 13, 2012. Thus, by transmitting the second RF signal, derived from or otherwise based on the first RF signal transmitted from portable MFS device 100, relay module 130 of FIG. 7 can also power a passive lead module 140.

A stimulation portion of the first RF signal encodes stimulus waveforms. This stimulation portion may be a later portion in a pattern being repeated in the first RF signal. The simulations portion of the first RF signal will be conditioned by stimulus conditioning circuitry 602 and further modulated by TX modulator 700 before transmission to implantable lead module 140. The stimulus waveforms contain short (e.g., about 0.5 ms or shorter) bursts of pulses. In one implementation, the first RF signal contains amplitude shift keying to indicate the end of the initial portion (for charging, e.g., capacitor 605) and the start of the stimulation portion. The amplitude shift keying may cause the stimulus conditioning circuitry 602 to generate a trigger to allow DC power to be received from the stored charge in capacitor 605. In another implementation, the stimulus conditioning circuit may include a counter that is set to expire upon a pre-determined number of pulse wave cycles. When the counted number of pulse cycles in the received first RF signal has reached the pre-determined threshold, the counter will expire and generate a trigger. Upon the trigger, stored charge in capacitor 605 may be harvested to power, for example, Tx modulator 700 and power amplifier 604. In either example implementation, the stimulus waveform is mixed with a carrier frequency of Tx modulator, the result is fed to power amplifier 604, and the output from the power amplifier 604 drives the Tx antenna 132 to transmit the amplified stimulus waveform modulated at the carrier frequency of Tx modulator 132 to the implantable lead module 140. As discussed above, the stored charge can be recharged by the next instance of the initial portion of the first RF signal received from portable MFS device 100.

In this mode, the carrier frequency of the first RF signal transmitted by the portable MFS device 100 can be decoupled from the carrier frequency of the stimulus waveform transmitted by the relay module 130. As long as the two carrier frequencies are sufficiently apart and the pass band of antenna 141 on implantable lead module 140 is sufficiently selective, the electrodes on the implantable lead module may only be driven by the stimulus waveform transmitted from relay module 130.

Figure 8:
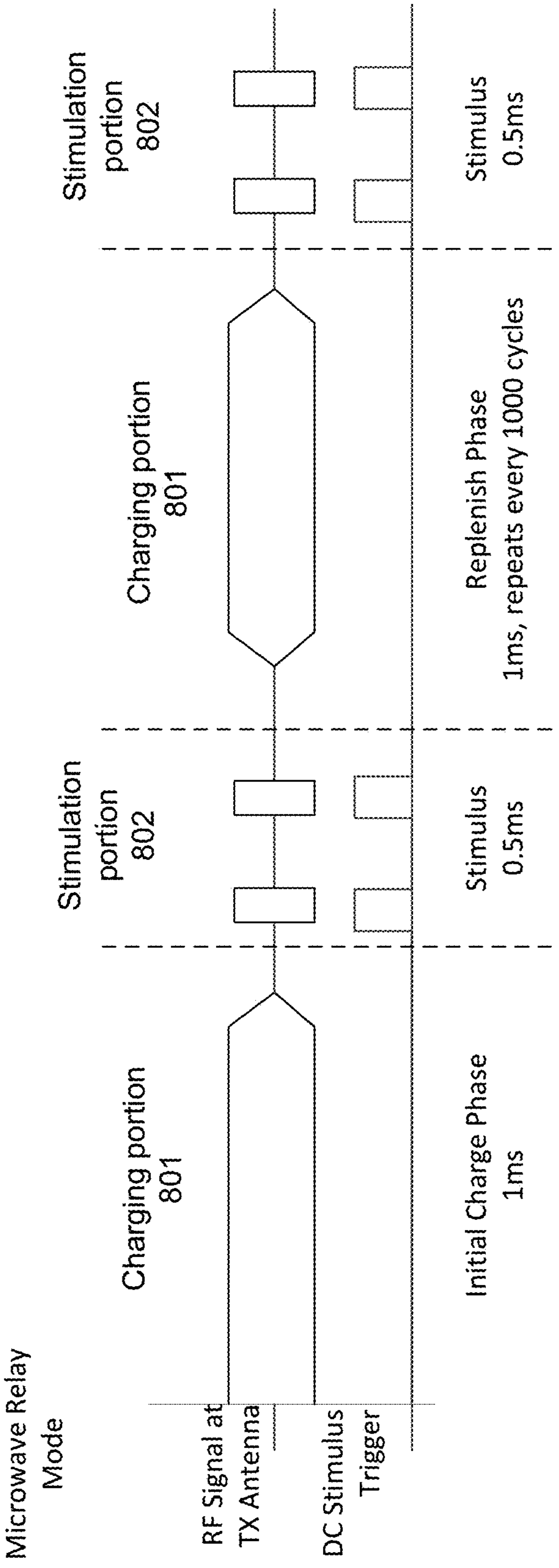
FIG. 8 is a timing diagram showing examples of the first RF signal received at the relay module 130 and subsequent waveforms generated by the flexible circuit.

FIG. 8 is a timing diagram showing examples of the first RF signal received at the relay module 130 and subsequent waveforms generated by the flexible circuit. For example, in microwave relay mode (illustrated in FIG. 6), the charging portion 801 utilized for charge storage may include a burst of pulses 1 millisecond or longer in pulse duration. Between each repetition of the charging portion of long bursts, a short burst, with pulse durations of 500 microseconds or less, encodes the stimulus waveforms. This portion is the stimulation portion 802. In one implementation, after every 1000 cycles of the short bursts, the stored power is recharged/replenished by the long bursts for pulse durations of 1 millisecond or longer. The cyclic pattern is repeated as needed to power the amplification circuitry on board the relay antenna module so that stimulus waveforms are sent to passive, implantable lead module 140.

Multiple implantable lead modules 140 may be implanted inside a subject's body. Multiple relay modules 130 may be configured to relay energy from a portable MFS device 100 to the implantable lead modules 140.

Figure 9:
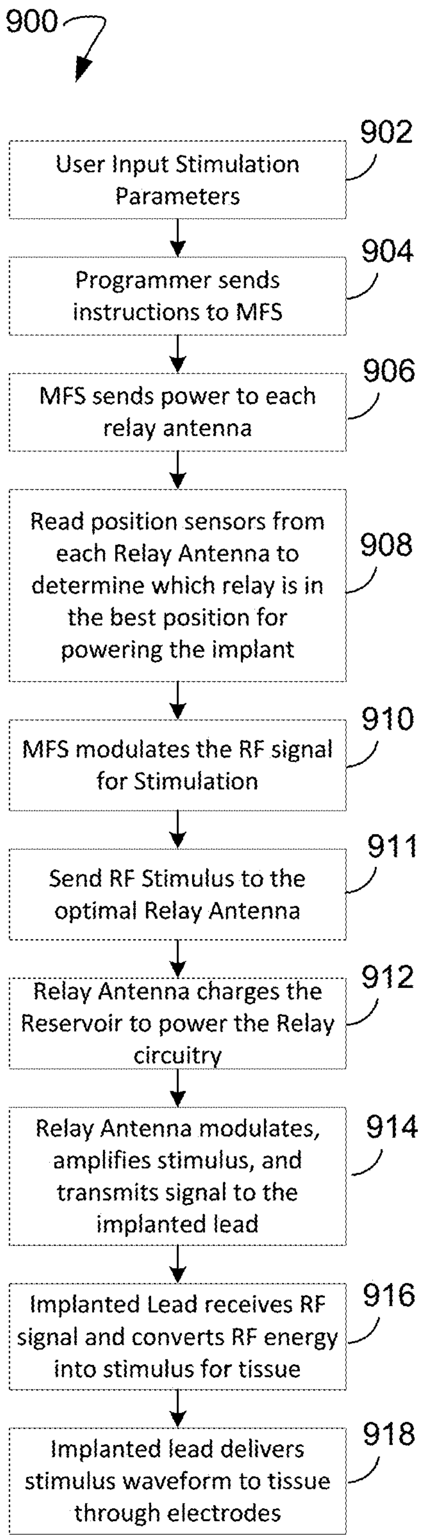
FIG. 9 is a flow chart showing an example process in which the wireless stimulation system selects a particular relay module.

FIG. 9 is a flow chart 900 showing an example process in which the wireless stimulation system chooses a particular relay module for relaying energy to a particular implantable lead module 140.

Initially, a user may input stimulation parameters into the portable MFS device 100 (902). The stimulation parameters may include, for example, frequency, amplitude, pulse width, treatment duration, etc. These parameters may be entered into portable MFS device 100 through a programmer module, e.g., UI 203 (904). Afterwards, the portable MFS device 100 may send power to each relay module 130 (906). As discussed below in FIGS. 10 and 11, each relay module 130 may include position sensors to provide positional information of the respective relay module 130. Example position sensors may include radio-frequency identification (RFID) devices, touch sensors, gyroscopes, etc.

Subsequently, the portable MFS device 100 may read the positional information generated by the position sensors at the respective relay module 130 (908). Based on the positional information collected, portable MFS device 100 may determine the relay module 130 best positioned to relay energy to power a particular implantable lead module 140. The relay module best positioned to relay energy may be the relay module with one of the following characteristics: the lowest amount of transmission loss, best coupling to tissue, closest proximity to the portable MFS device 100, or closest proximity to a particular implantable lead module 140. For example, a software algorithm may be implemented on the portable MFS device 100 to determine the position of a particular relay module 130 relative to a given implanted implantable lead module 130. The portable MFS device 100 may then determine which relay module should be selected to transmit energy most efficiently to the given implanted implantable lead module 130. In this example, the relay module that will transmit energy most efficiently to the given implantable lead module may be the relay module closest to the given implantable lead module. The portable MFS device 100 can digitally control a multiplexor to selectively transmit energy to a chosen relay module 130.

Thereafter, the portable MFS device 100 may generate the first RF signal by modulating a carrier signal with a particular stimulation waveform, for example, according to stimulation parameters stored in memory 211 (910). The portable MFS device 100 may then send the first RF signal to the optimal relay module as determined above (911). The selected optimal relay module may be the only relay module activated to receive the first RF signal. The activation may be achieved remotely by portable MFS device 100 before transmission of the first RF signal.

When the selected optimal relay module receives the first RF signal at its Rx antenna 131, the relay module may utilize a charging portion of the received first RF signal to charge a reservoir, such as, for example, capacitor 605, and then utilize the stored charge to power the relay circuitry (912). For example, the stored charge may be used to modulate a carrier wave with a stimulation waveform, amplifier the modulated carrier wave to provide the second RF signal, and then transmit the second RF signal to the given implantable lead module (914).

Subsequently, the given implantable lead module receives the second RF signal. As a passive device, the given implantable lead module is powered by the energy contained in the second RF signal and extracts the stimulation waveform from the received second RF signal (916). In capturing the energy contained in the second RF signal, the implantable lead module 140 may store a charge in a capacitor. The stored charge will be utilized to apply the extracted stimulation waveform to the electrodes 322 (918).

Figure 10:
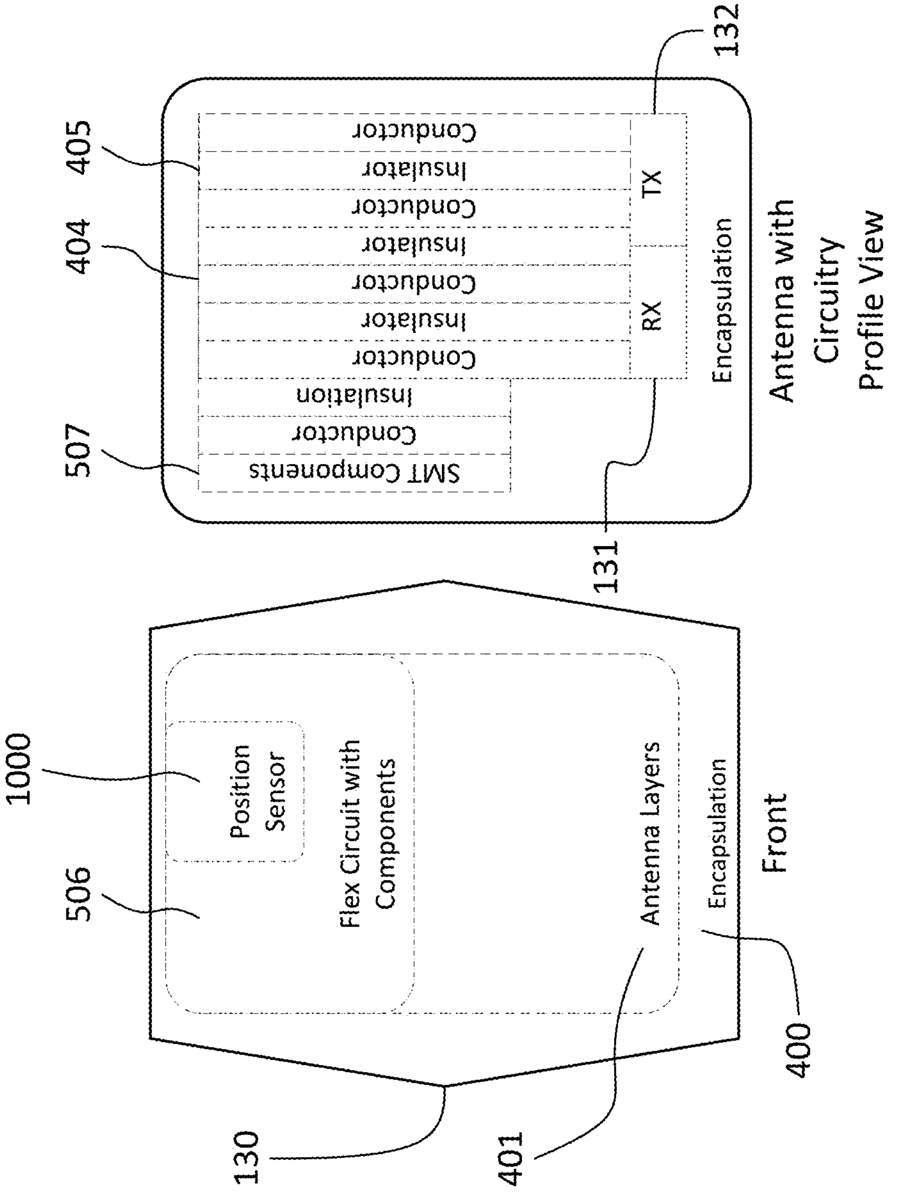
FIG. 10 shows example of a configuration of the relay module with a position sensor.

FIG. 10 shows an example of a configuration of a relay module 130 with a position sensor 1000. As illustrated, position sensor 1000 may be integrated on flexible circuit 506. As shown in the left panel of FIG. 10, the flexible circuit 506 may be placed on top of antenna layers 401 and occupying part of the surface area of antenna layers 401. Encapsulation material 400 may enclose flexible circuit 506 (with components) and antenna layers 401, as discussed above.

The right panel shows a profile view of the example configuration of relay module 130 with positional sensor 1000. Position sensor 1000 may be a component of the surface mount (SMT) components 507 mounted on flexible circuit 506. As discussed above, the Rx antenna 131 and the Tx antenna 132 may be implemented as patch-on-patch antennas. The Tx antenna 132 of each relay module 130 can be circularly polarized to substantially obviate directional dependence, thereby permitting a wider acceptance angle at the antenna 141 on implantable lead module 140.

In one implementation, a semiconductor gyroscope can be used as a position sensor to determine the orientation of Rx antenna 131 and Tx antenna 132. In other implementations, touch sensors can be used as a position sensor to detect, for example, if the Tx antenna 132 of the relay module 130 is coming in contact with an object. The touch sensor may also detect any force gradients to determine whether the side of Tx antenna 132 is touching something pliable, such as clothing, or something hard. In particular, when Tx antenna 132 is touching a lossy surface, like the thigh, it could be considered a worst case scenario. A lossy surface may have different impedance than the impedance of the antenna. When the Rx antenna 131 or the Tx antenna 132 is touching a side pocket material, or other clothing, antenna coupling could be closer to that of air coupling, which may be considered the best-case scenario.

In yet other implementations, an additional coupler can be used to detect the forward power and reflection outputted by a given Tx antenna 132. A lossy surface may be detected when the measured reflection measurement is high, such as, for example, over 25% of the transmission energy. The presence of a lossy surface on a particular relay module may provide feedback to portable MFS device 100 that the particular relay module should be avoided. As a result, an alert may be provided to UI 203 on portable MFS device 100 to notify a user of the situation. Unless the situation has been remedied, the portable MFS device 100 may refrain from using the given relay module to relay energy to an implantable lead module.

Figure 11:
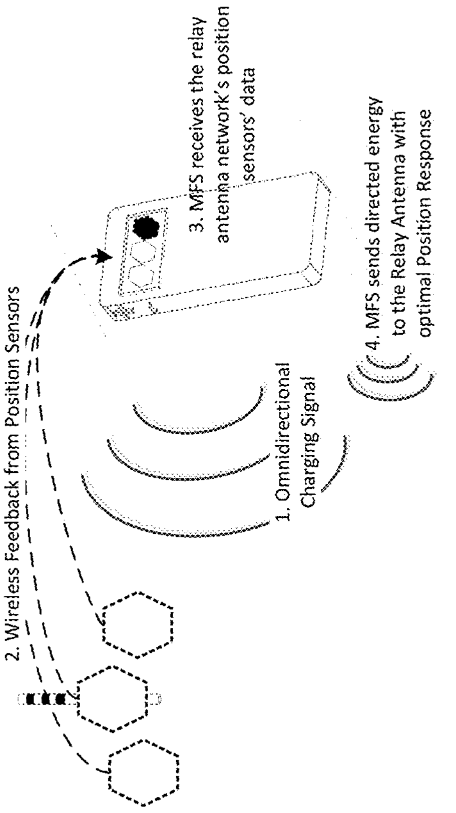
FIG. 11 illustrates an example workflow of a wireless stimulation system with the relay module of FIG. 10.

FIG. 11 illustrates an example workflow of a wireless stimulation system with the relay module 130 of FIG. 10. In step 1, the portable MFS device 100 transmits omnidirectional charging signal to all relay modules in range. In step 2, position sensors on the relay module 130 provide positional readings for the host relay module and utilize a telemetry antenna within the relay module to transmit the positional information to the portable MFS device as a feedback signal from the position sensors. In some implementations, Rx antenna 131 may serve as a transceiver to transmit the telemetry signal to the portable MFS device 100. In these implementations, relay module 130 may include a power source, such as, for example, a rechargeable battery. In step 3, the portable MFS device 100 receives the information from the position sensors on the respective relay modules. Based on the positional information received, the portable MFS device 100 software algorithms determine which relay module 130 is in the most optimal position to relay the maximum amount of energy to power a given implantable lead module 140 that has already been implanted in the subject, as discussed above. In step 4, portable MFS device 100 sends energy directed to the chosen relay module 130. Thereafter, the relay module 130 harvests the energy to power the given implantable lead module 140, as discussed above.

Figure 12A:
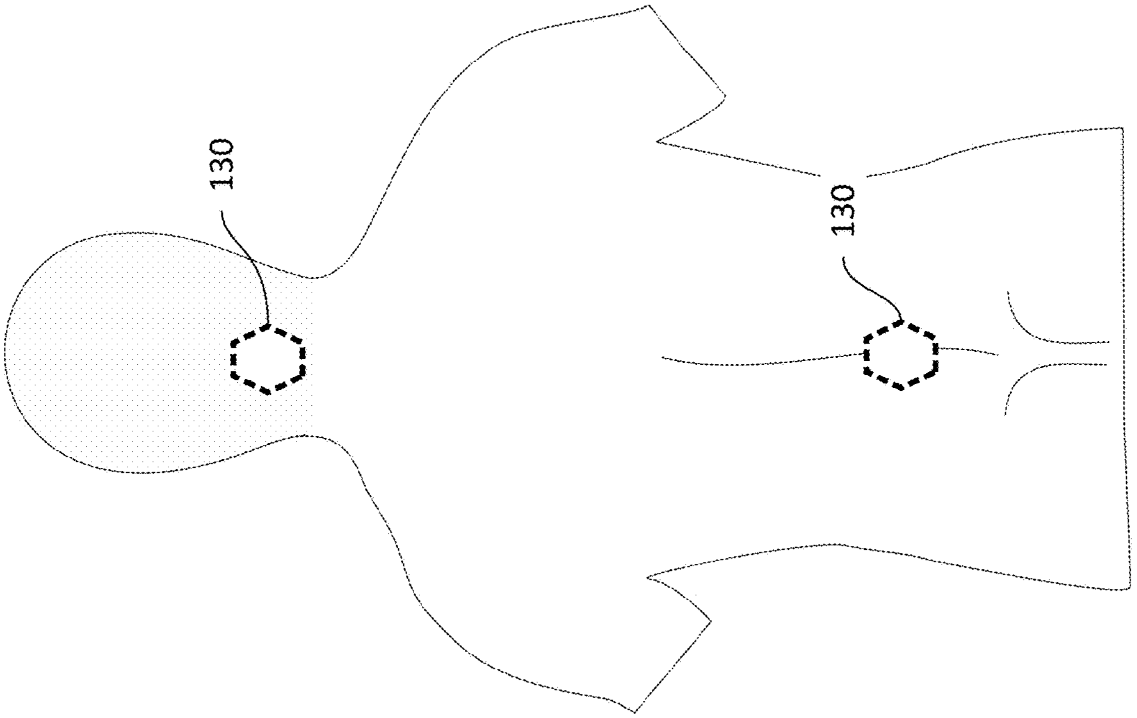
FIG. 12A-E show example placements of the relay module.
Figure 12B:
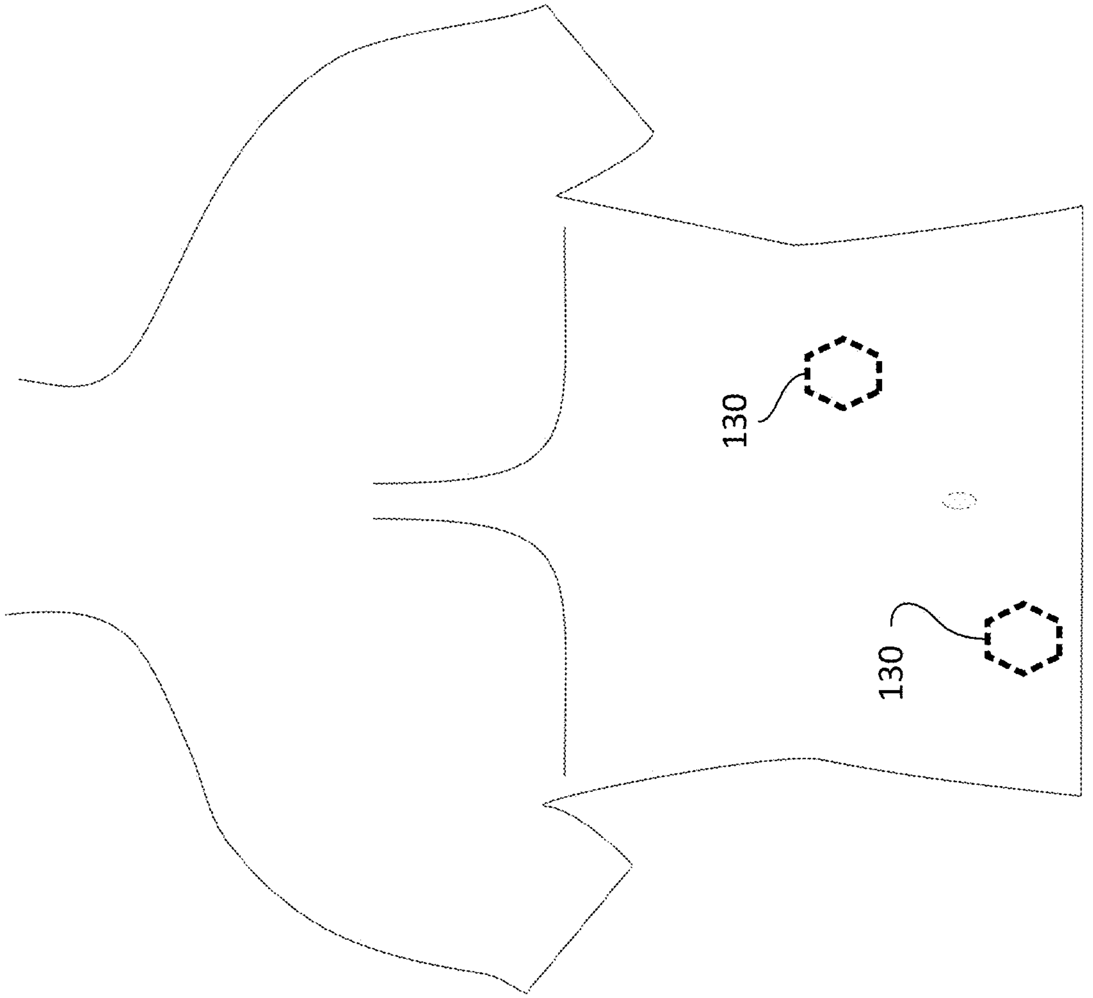
Figure 12C:
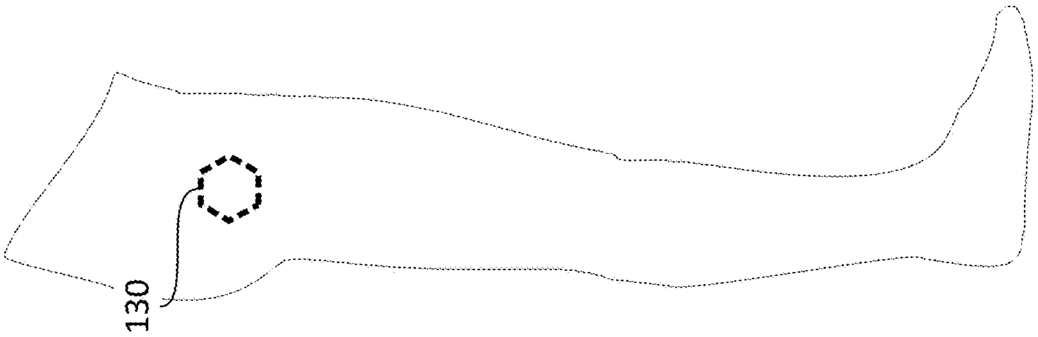
Figure 12D:
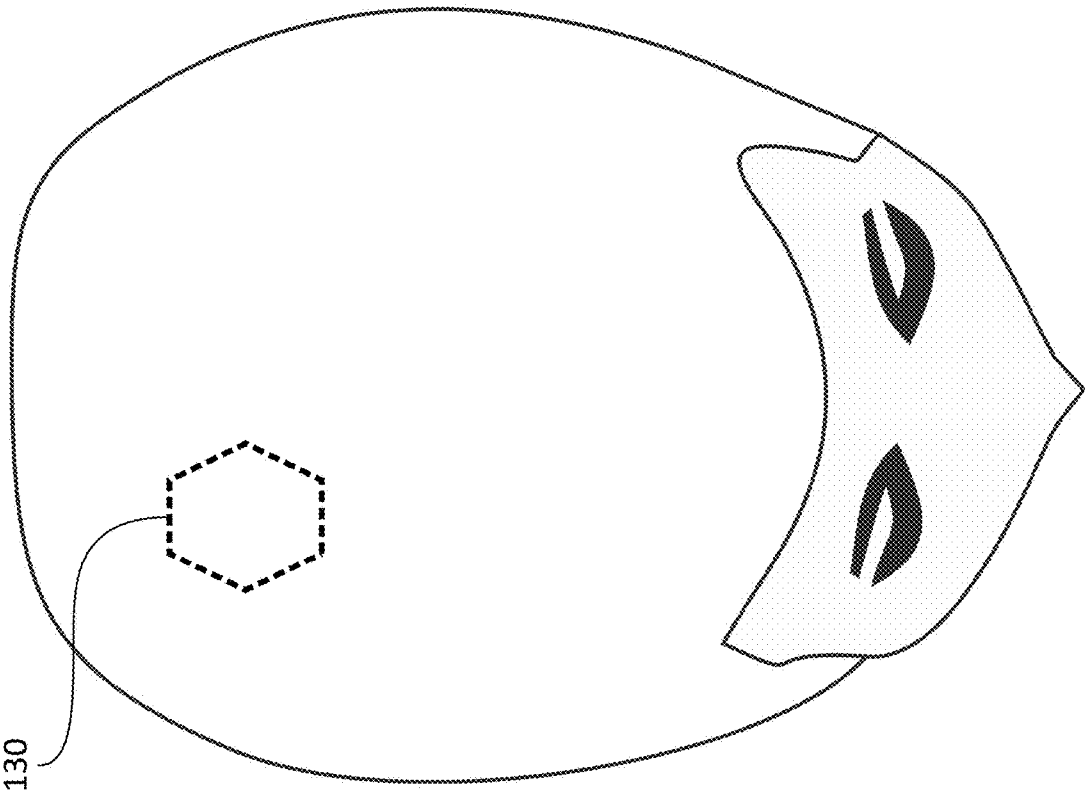
Figure 12E:
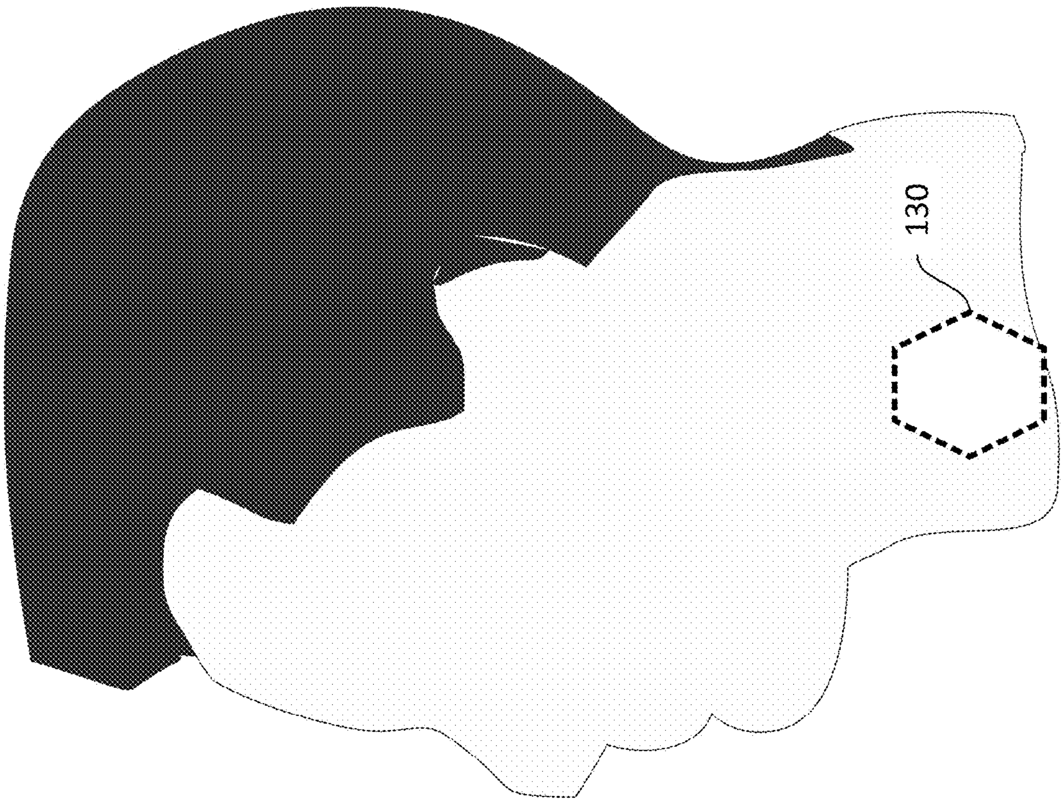

FIG. 12A-E show example placements of the relay module. The relay module 130 can be placed nearby a variety of anatomical targets that contain the implanted lead module. Example targeted sites for relay module 130 include, but are not limited to, behind the neck or at the small of the back as shown in FIG. 12A; the waistline or abdomen, as shown in FIG. 12B; the side of the buttock as shown in FIG. 12C. The relay module 130 may also be placed under the skin in the skullcap, as illustrated in FIG. 12D, and just under the skin over the vagus nerve around the neck area, as illustrated in FIG. 12E.

Figure 13A:
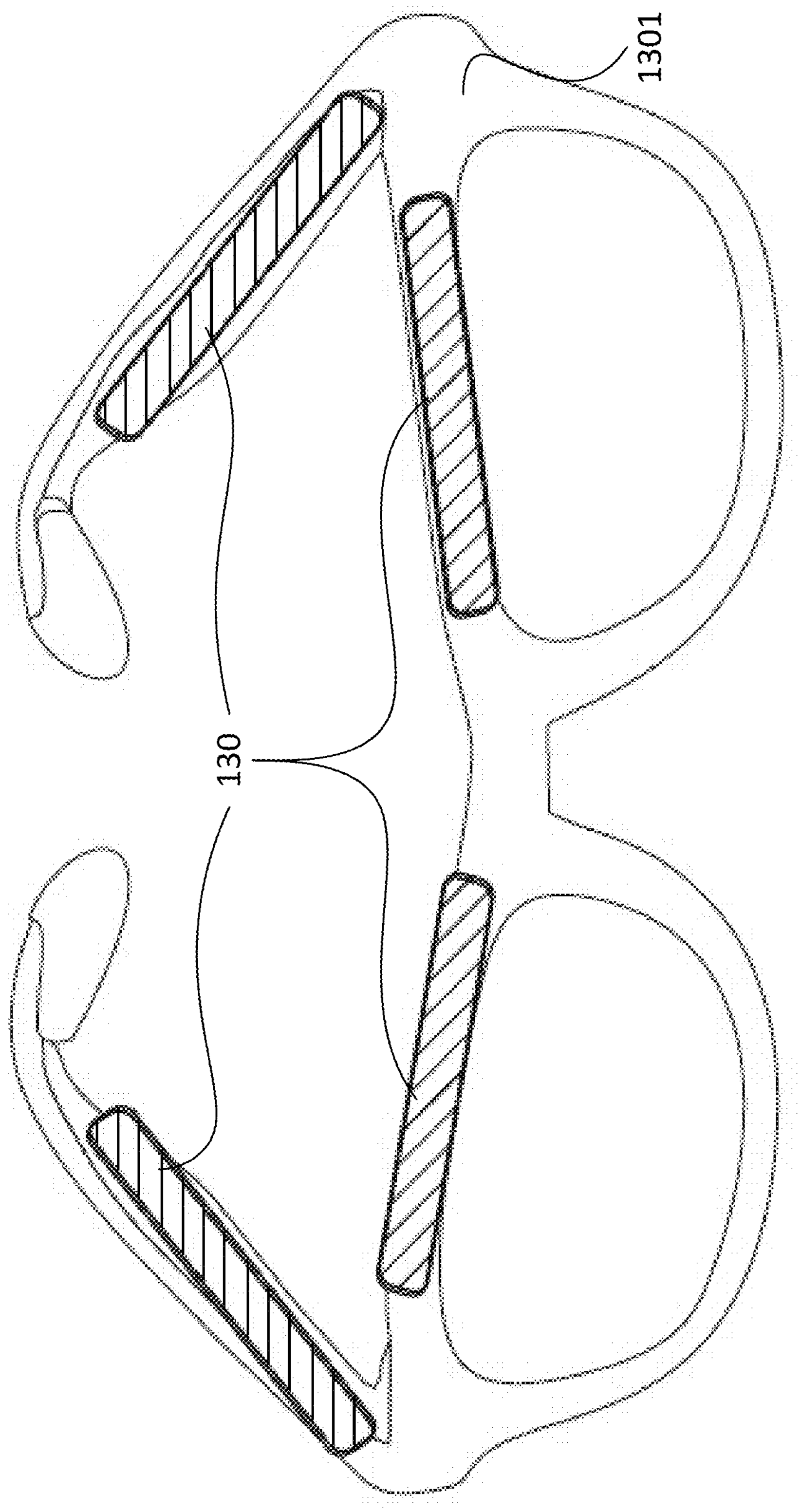
FIG. 13A-L show example placements of the relay module as a wearable item.
Figure 13B:
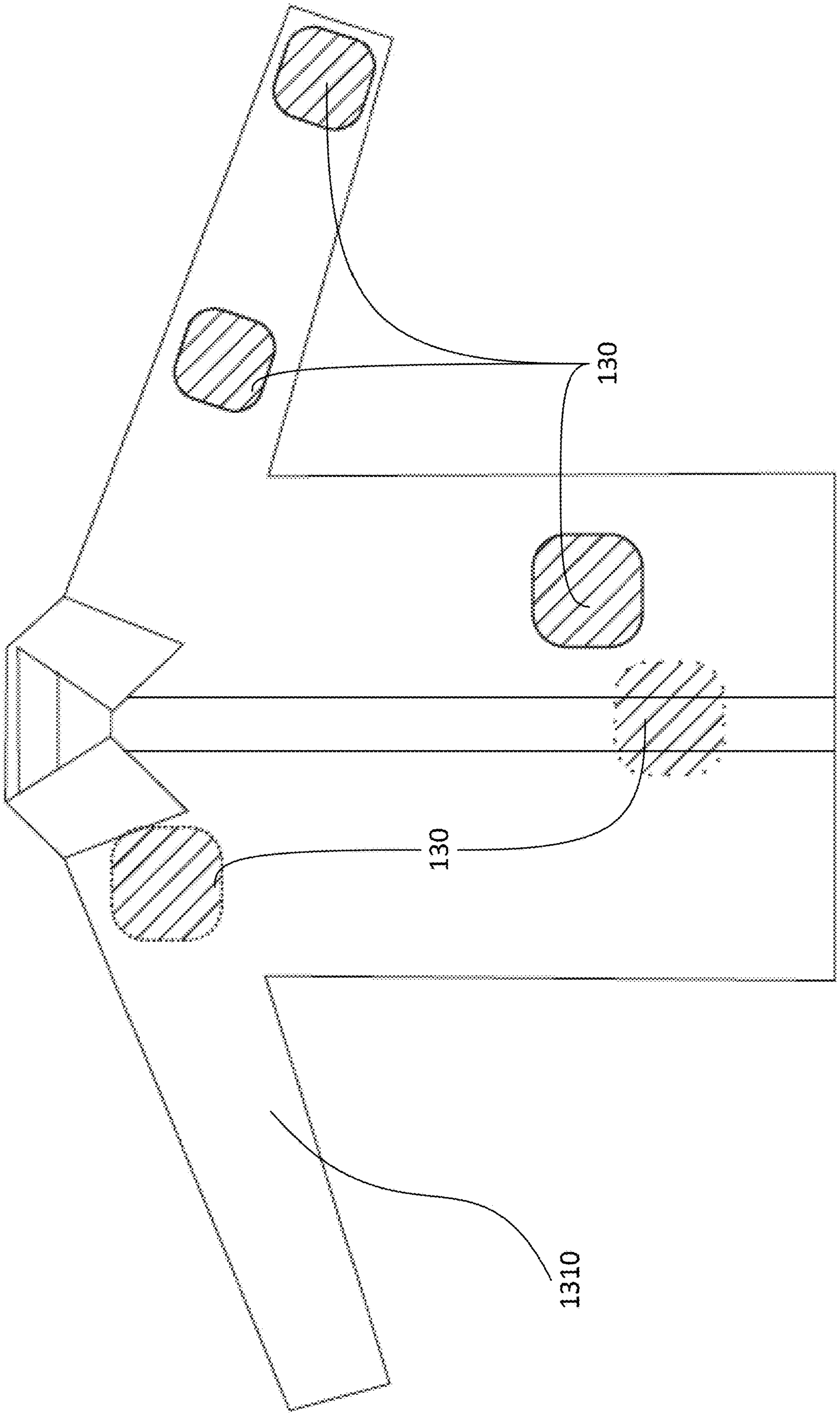
Figure 13C:
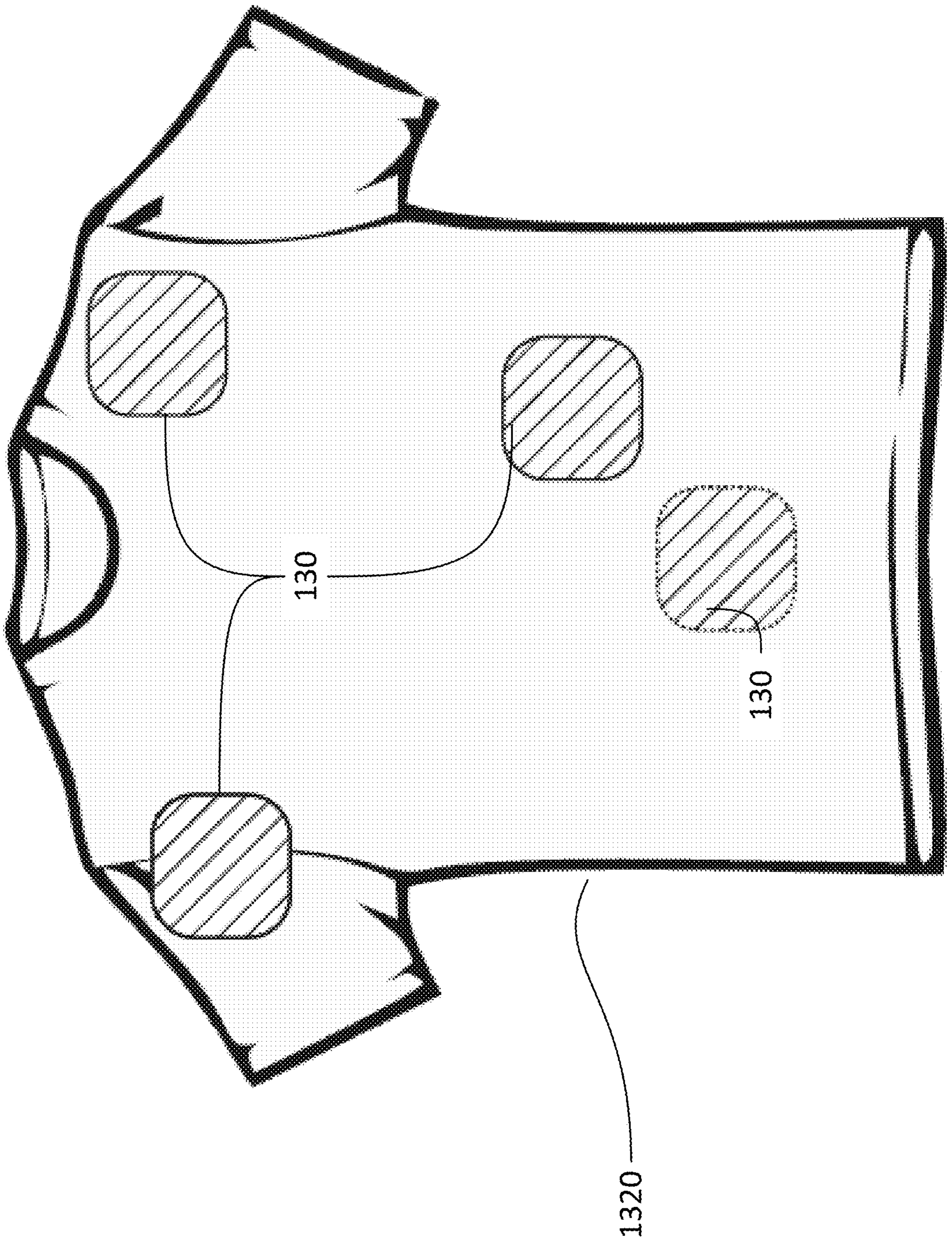
Figure 13D:
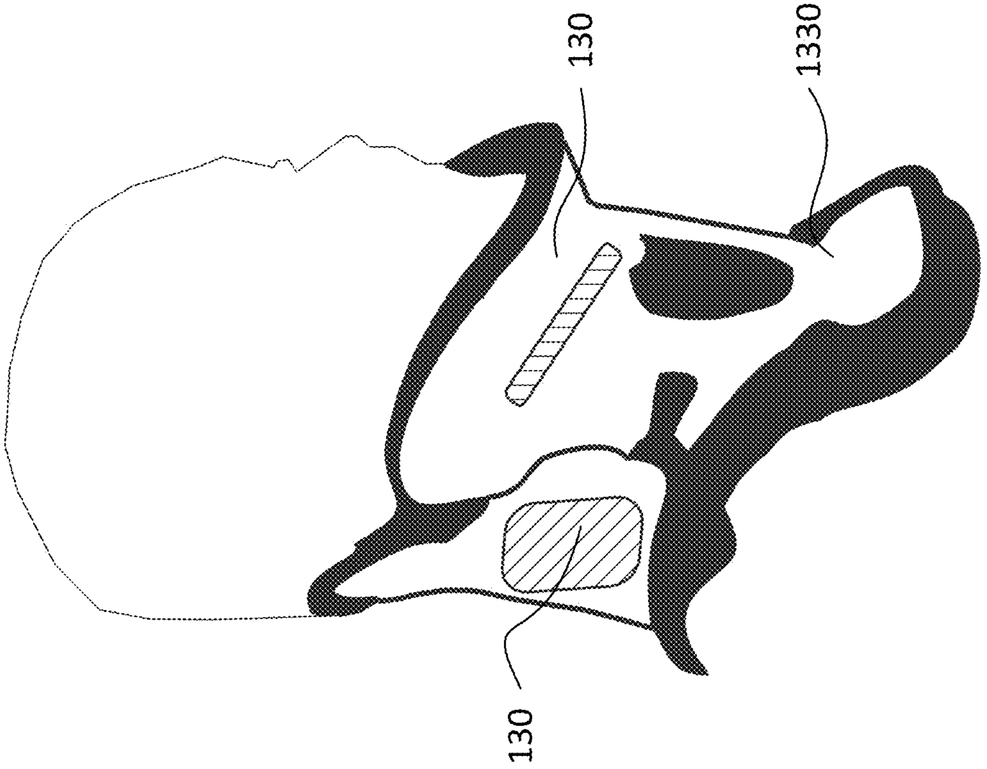
Figure 13E:
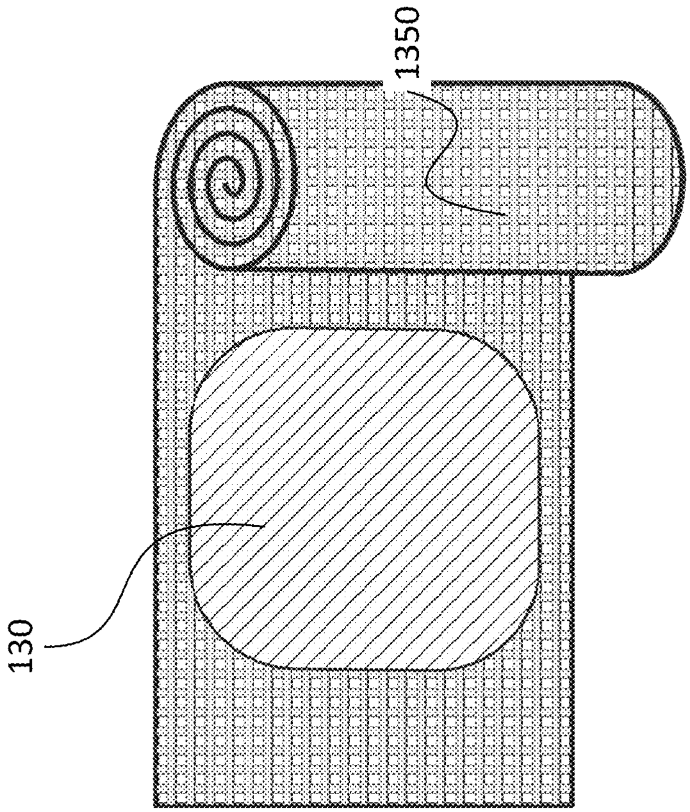
Figure 13F:
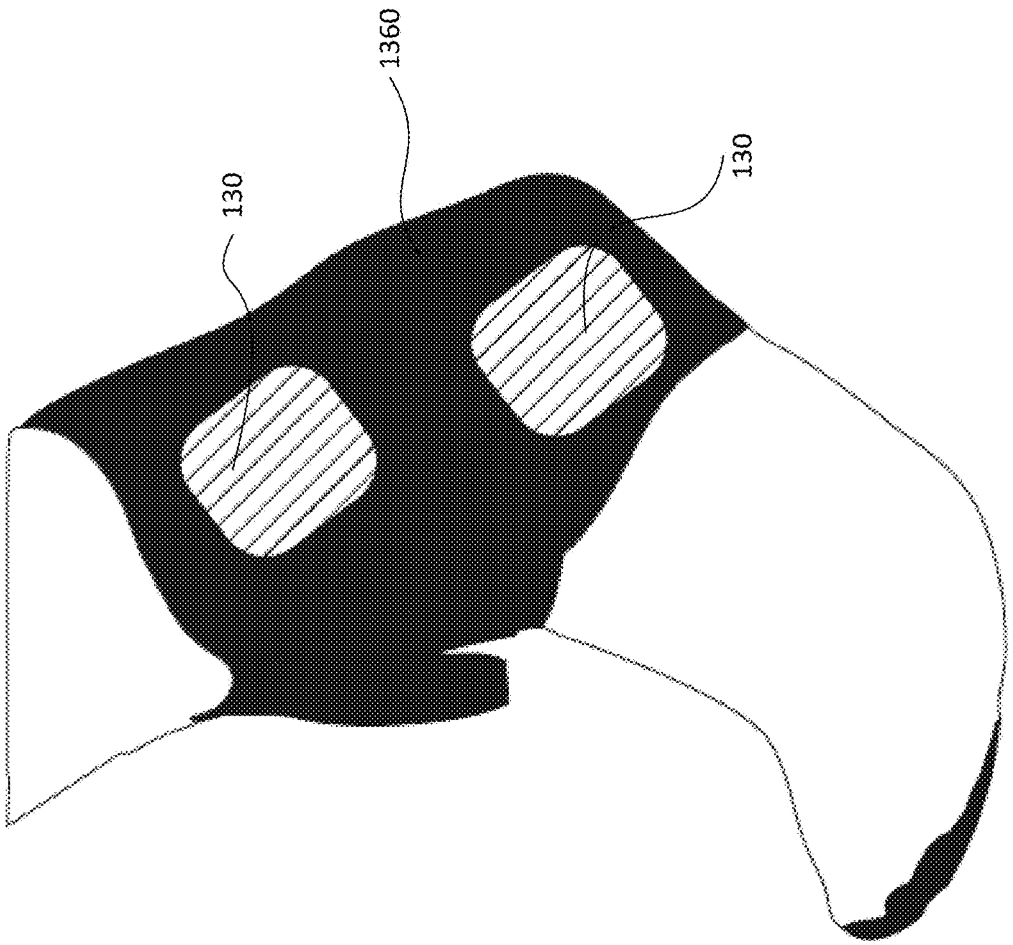
Figure 13G:
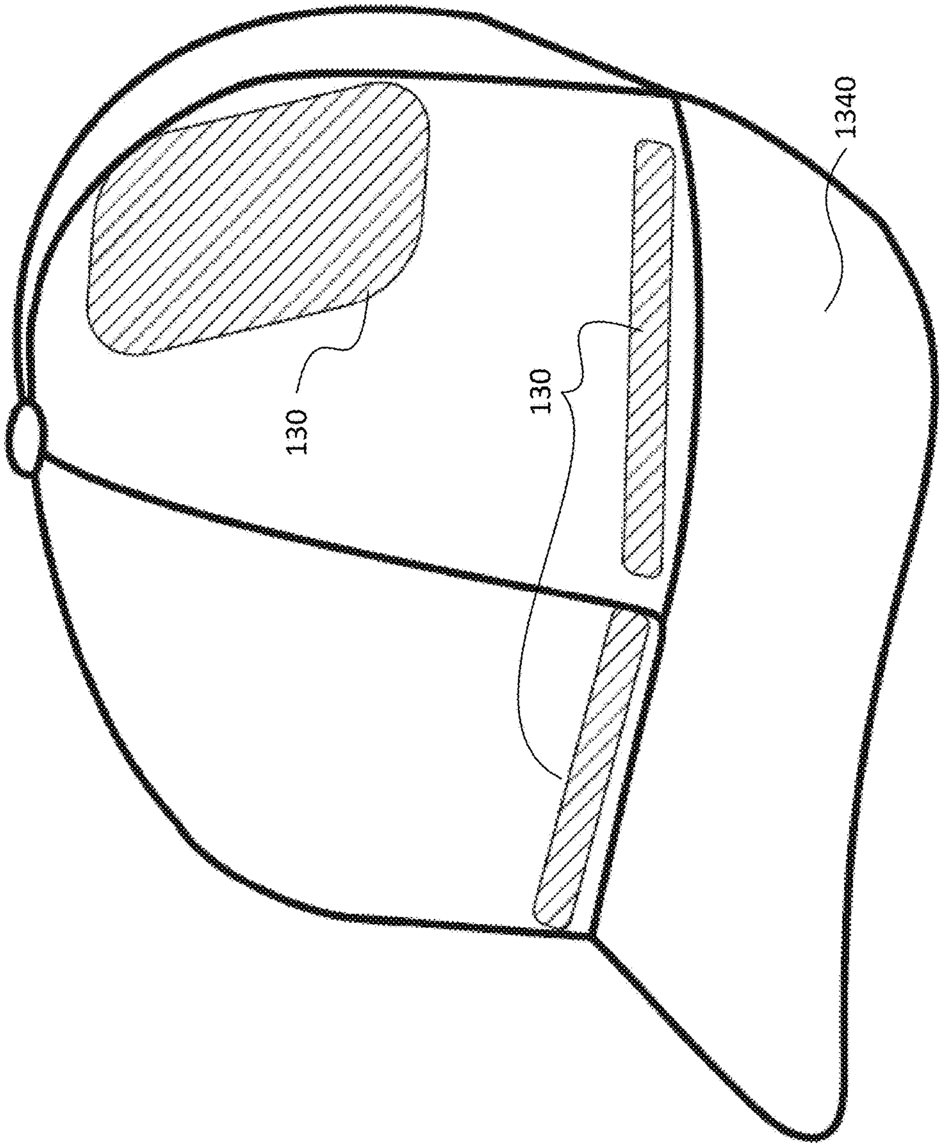
Figure 13H:
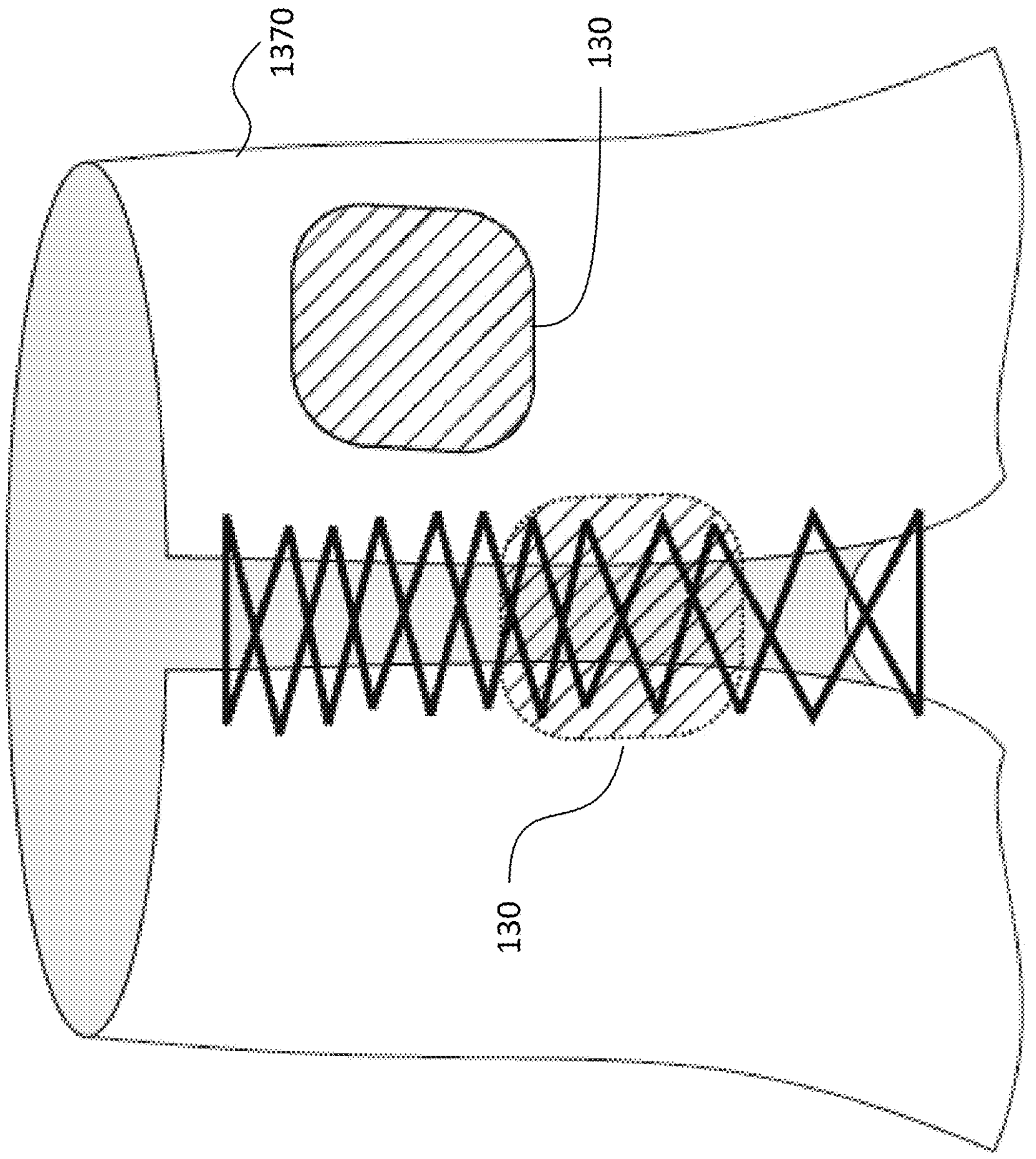
Figure 13I:
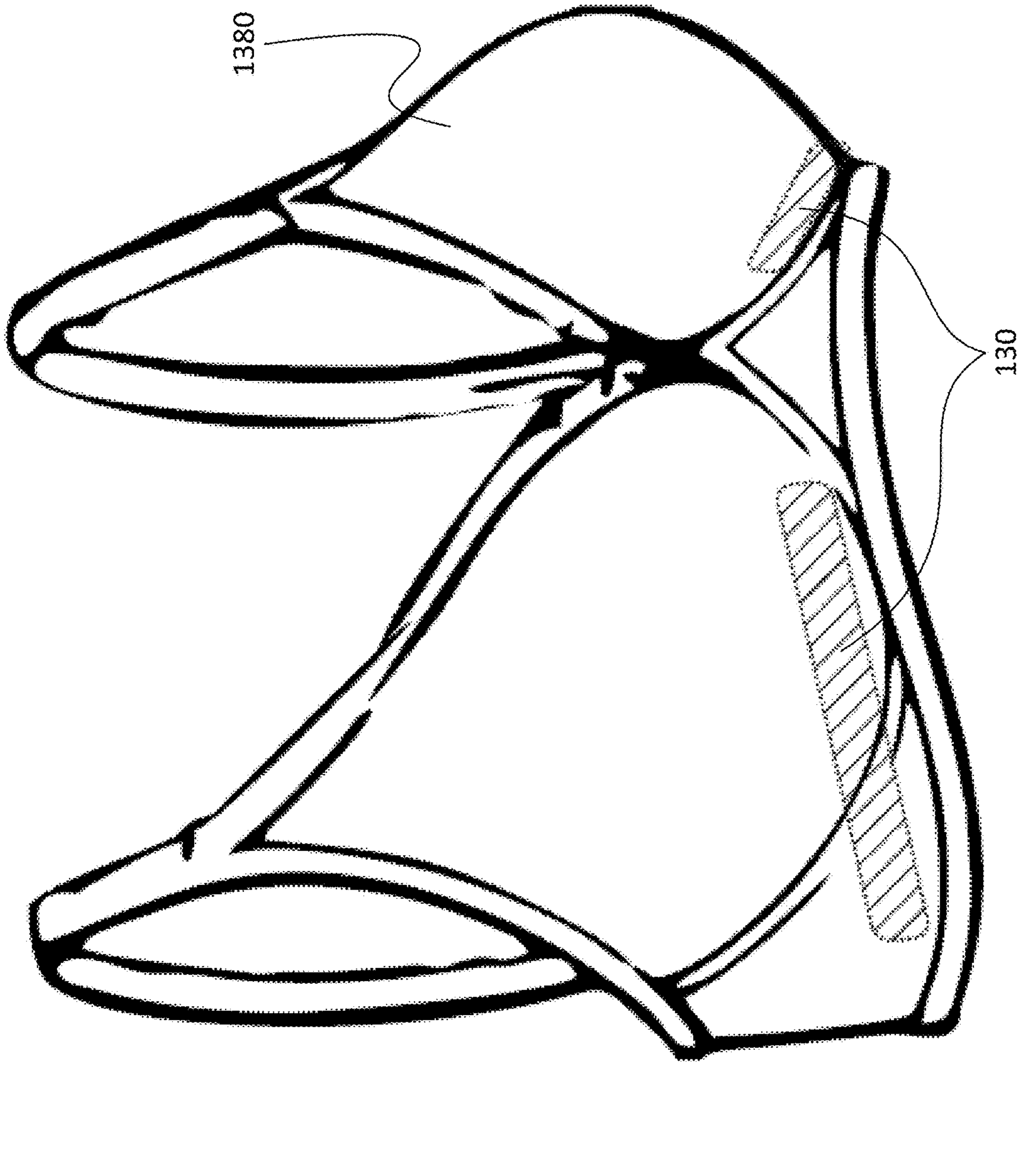
Figure 13J:
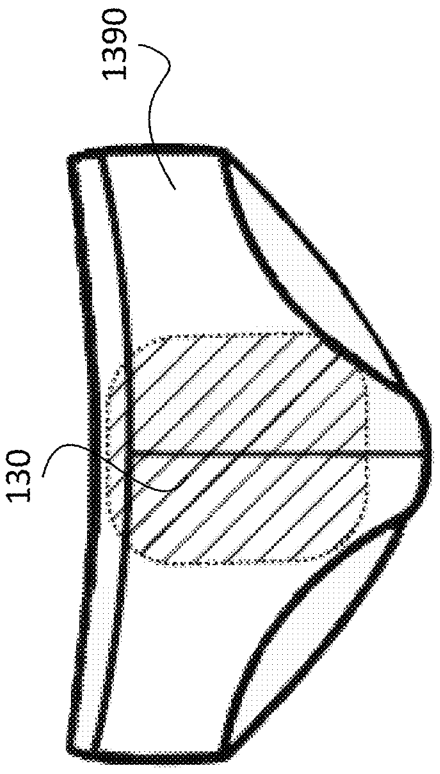
Figure 13K:
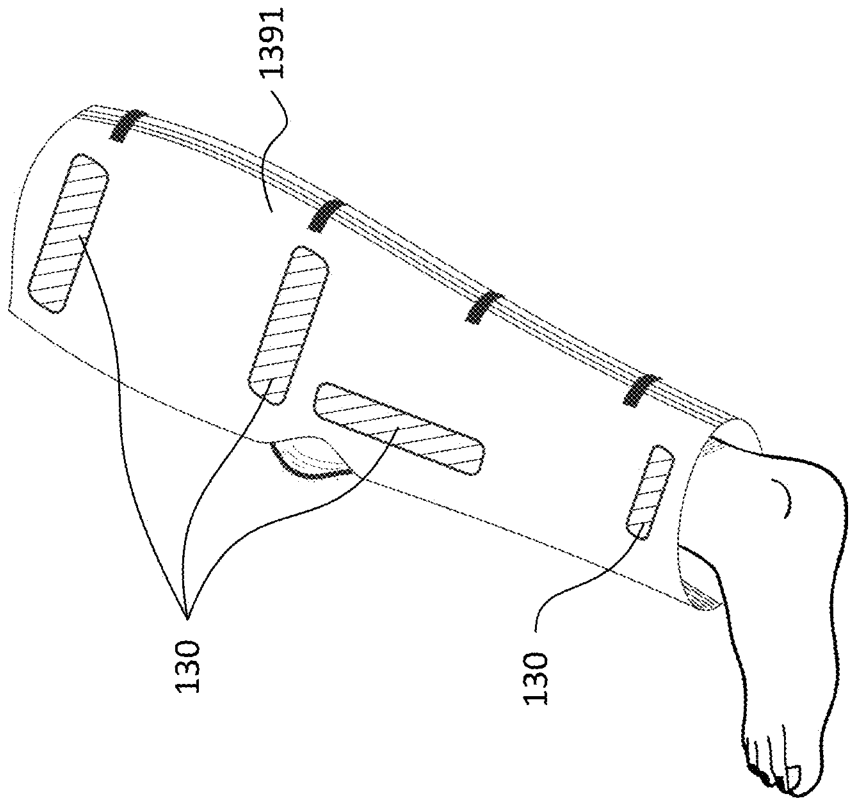
Figure 13L:
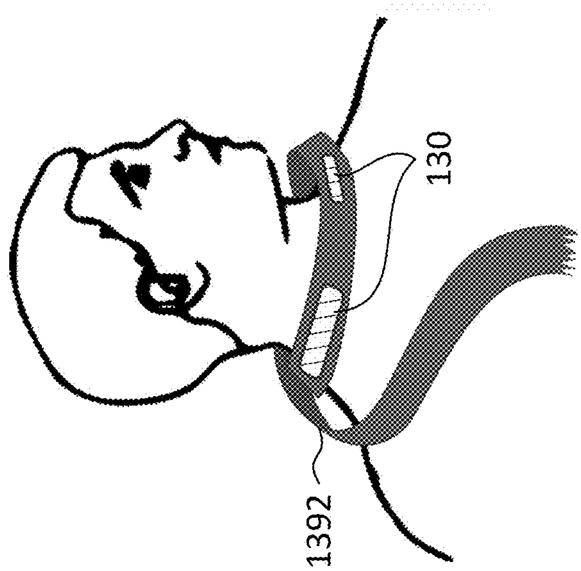

FIGS. 13A-L show example placements of the relay module as a wearable item. Relay module 130 may be placed, for example, a bandage, a strap, an adhesive surface, a sleeve cover, or a piece of cloth worn on the body, for instance behind the neck or at the small of the back. FIG. 13A shows an example placement of relay module 130 in an eyeglass frame 1301. FIG. 13B depicts a dress shirt 1310 with relay modules 130 attached to the inside and outside. FIG. 13C depicts relay module 130 placed on the inside and outside of a general use shirt 1320. FIG. 13D depicts an example placement of relay module 130 in a neck brace or other stabilization brace 1330. FIG. 13E shows example placement of relay module 130 in a ball cap 1340. FIG. 13F shows example placement of relay module 130 PR on a flexible ace bandage 1350 housing which can be utilized at a multitude of locations on the body. FIG. 13G shows example placement of relay module 130 on an ankle brace 1360. FIG. 13H d shows an example of placing relay module 130 within a girdle or haulter 1370. FIG. 13I shows example placement of relay module 130 on the body of a bra structure 1380. FIG. 13J shows example placement of relay module 130 on trunks 1390. FIG. 13K depicts example placement of relay module 130 in multiple locations on a leg brace 1391. FIG. 13L depicts example placement of relay module 130 within a scarf material 1392.

The design of the relay module 130 is intended to be convenient for patient use in daily activities such as exercise, working, and other leisure activities. A strap holding the relay module 130 over an implanted antenna 141 on implantable lead module 140 can become inconvenient in situations such as swimming, such as where the relay module 130 can shift, for example, during the sleeping time of the subject; or where the relay module 130 could press against the skin potentially uncomfortably. Additionally, bulky medical devices tend to be unaesthetic and are undesirable in many situations where skin is exposed.

The implementations discussed above address these issues by placing the pulse generator on the portable MFS device 100 wirelessly away from the body up to three feet. The implementations utilize a compact relay module 130 that may seamlessly integrate into a wearable item or be subcutaneously placed. The relay module 130 may relay energy received from portable MFS device 100 to power implantable lead module 140. Some implementations may further detect which relay module is in contact with lossy materials and guides the pulsed microwave energy from portable MFS device 100 to be directed to the relay module with the best coupling to a particular implantable lead module.

FIG. 14A-14D show example configurations of a portable MFS device. As discussed above, the portable MFS device 100 may be typically located outside the body and is not physically connected to the skin; however can be located subcutaneously (not shown). In certain embodiments, a programmer is embedded into the portable MFS device 100 that interfaces with a user to provide options to change the frequency, amplitude, pulse width, treatment duration, and other system specifications. In certain circumstances, a manufacturer's representative will set specific parameters for the MFS device and the patient will be given the option to adjust certain subsets of those parameters, within a specified range, based on a user's experience.

Figure 14A:
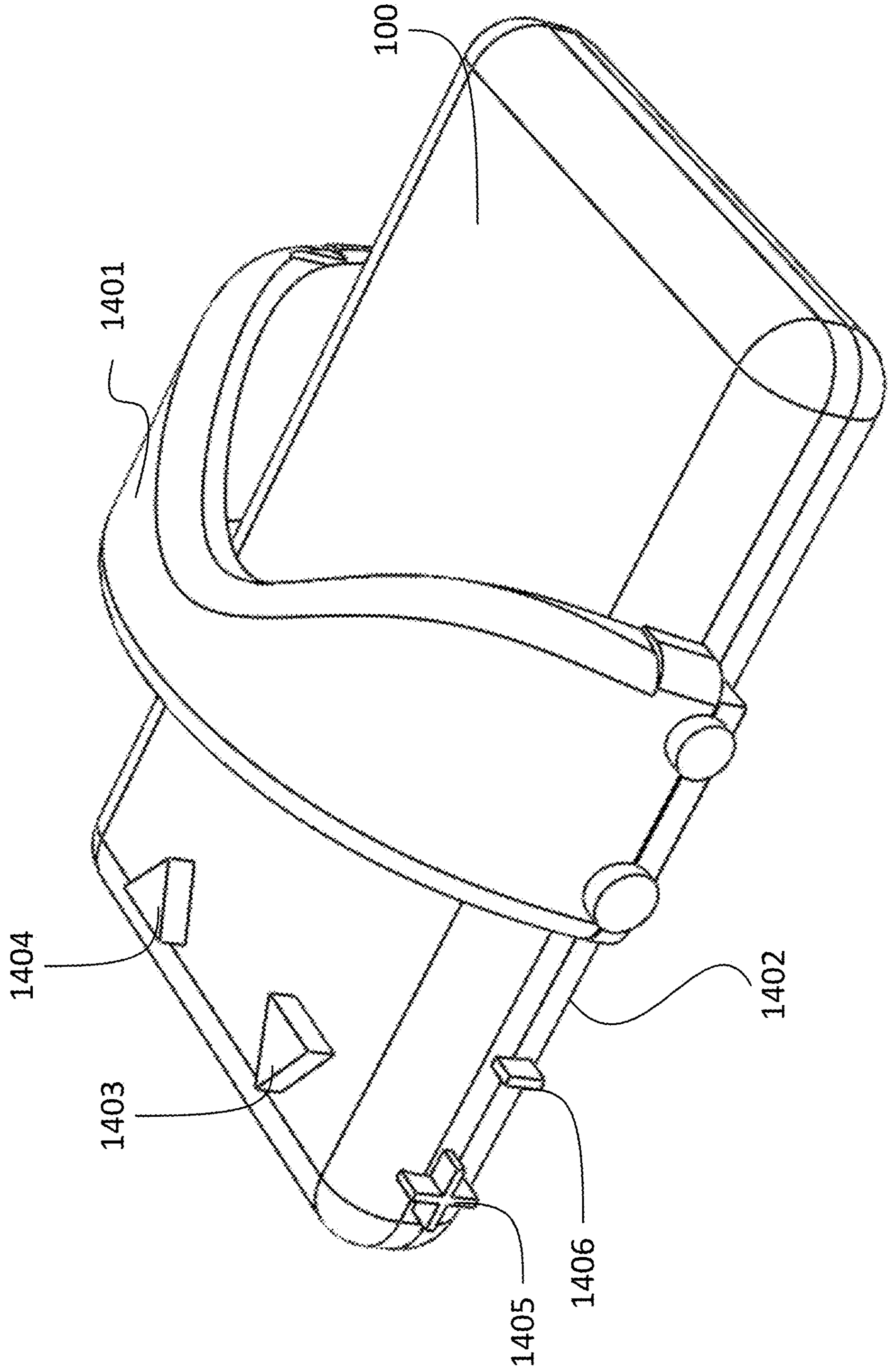
FIG. 14A-14D show example configurations of a portable MFS device.
Figure 14B:
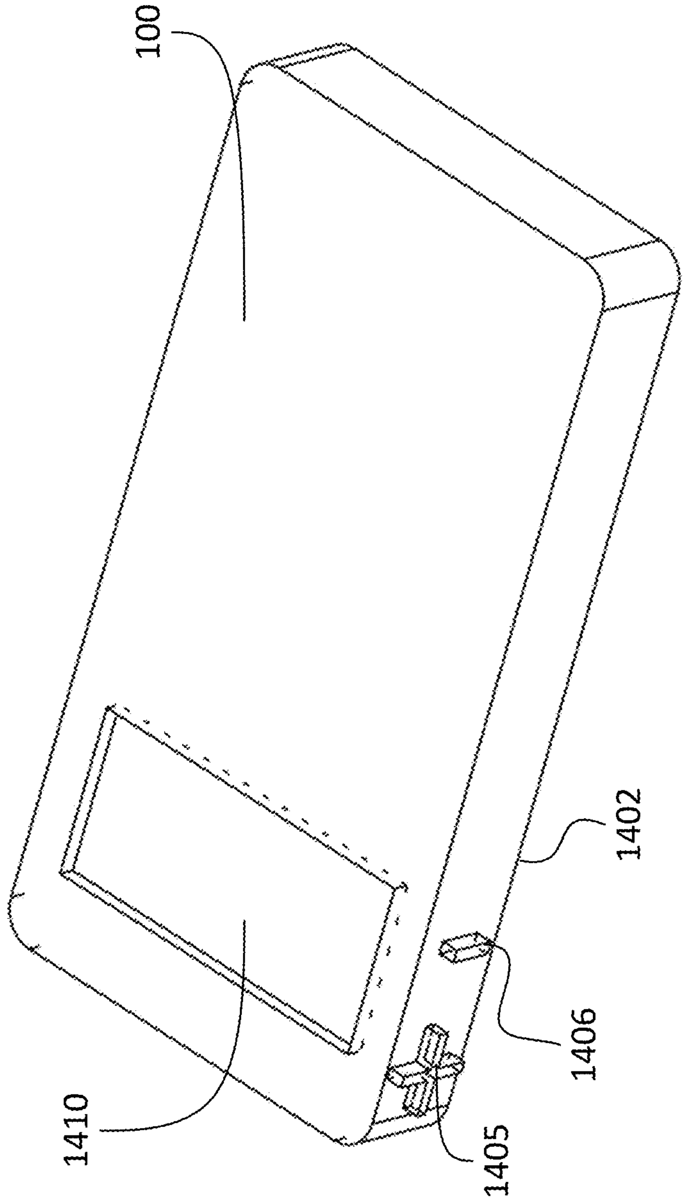
Figure 14C:
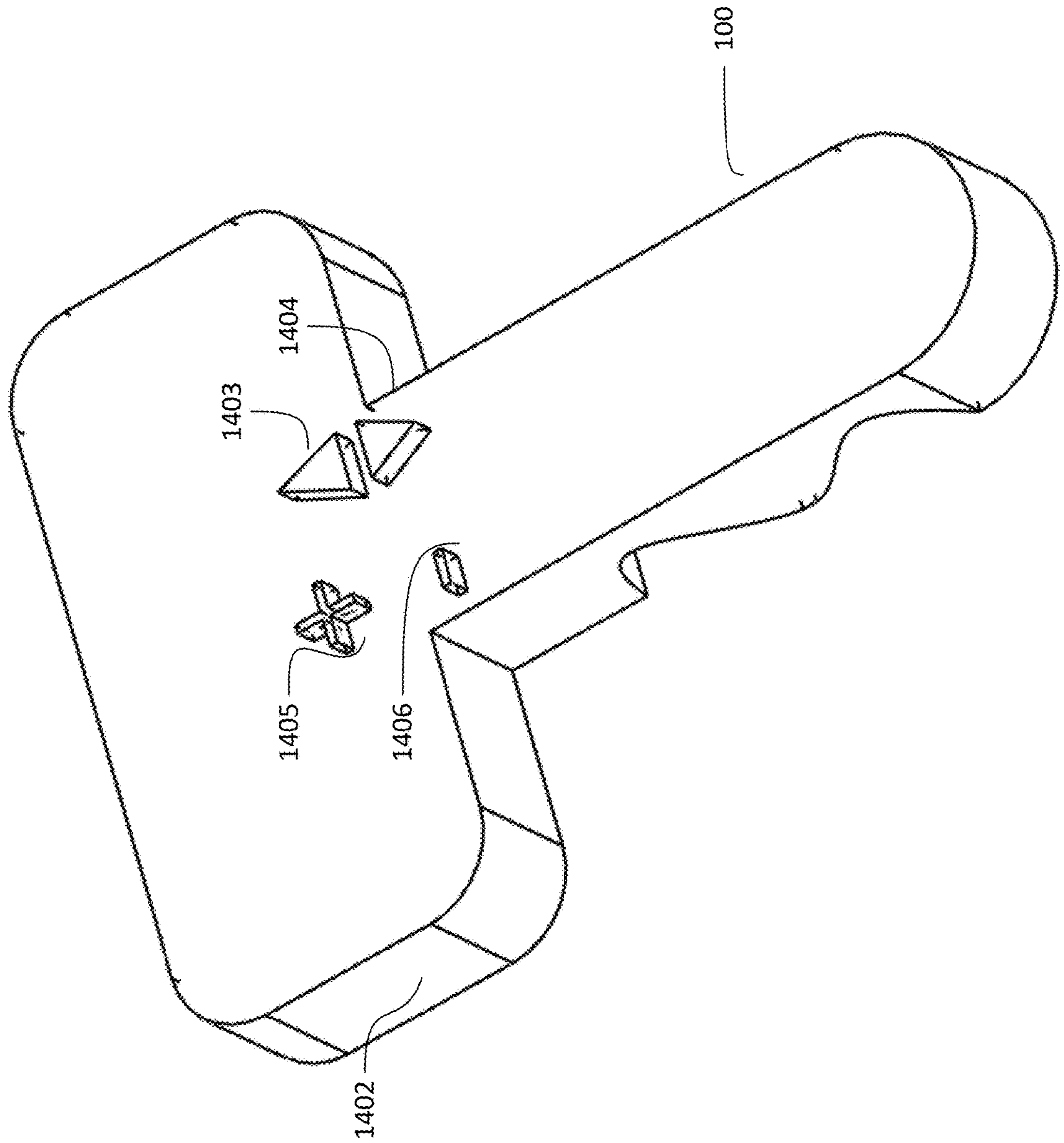
Figure 14D:
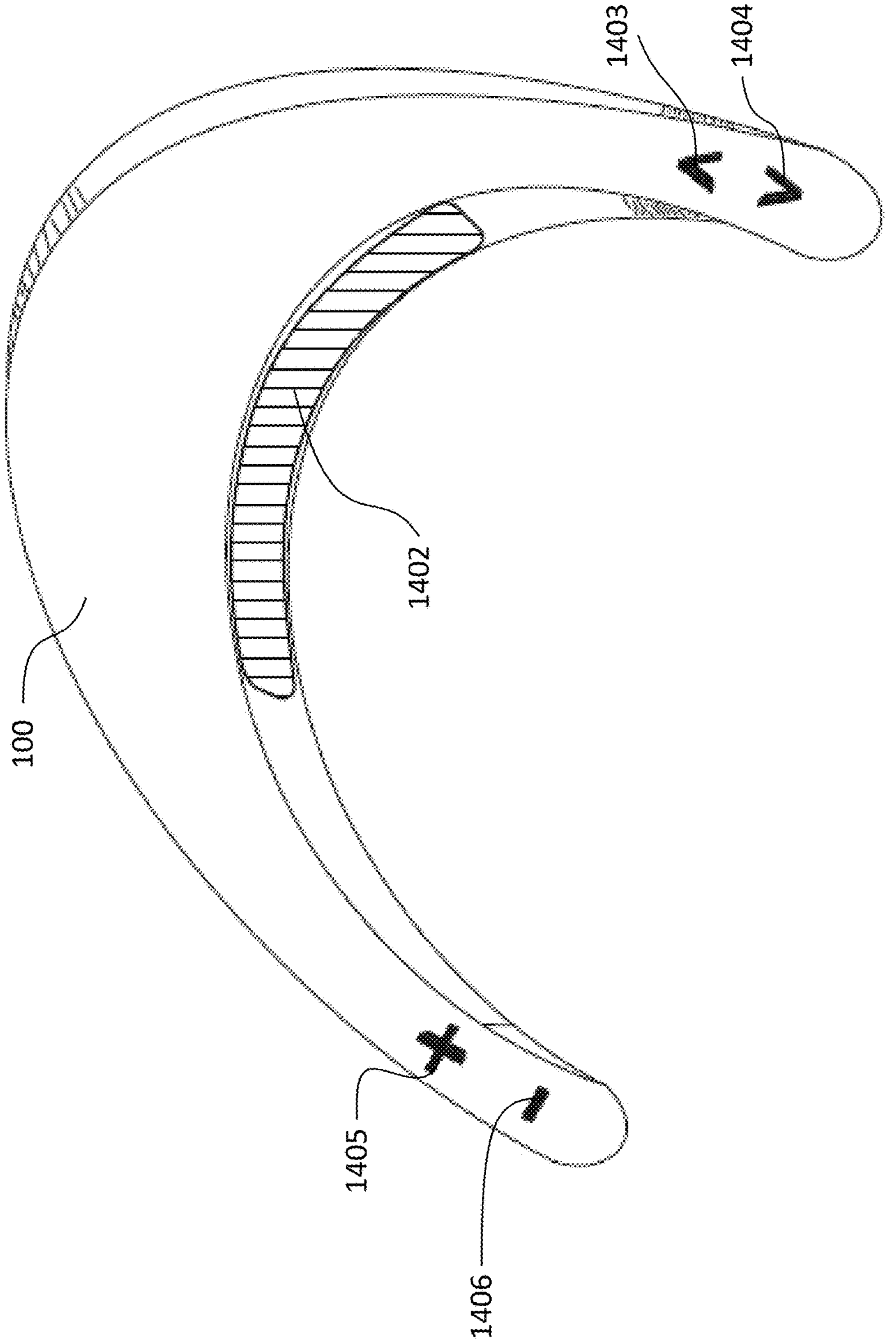

FIG. 14A shows an example portable MFS device 100 with a strap 1401, surface 1402, and control buttons 1403-1406 for a user to make adjustments to the stimulation parameters. Antenna 110 may be mounted under surface 1402. FIG. 14B shows another example portable MFS device 100 with a display 1410 on surface 1402, and control buttons 1405 and 1406. Antenna 110 may be mounted under surface 1402. The display 1410 may provide visual information to a user about the progress of the therapy and associated stimulation parameters. Control buttons 1405 and 1406 may allow a user to make adjustments to the stimulation parameters. FIG. 14C shows yet another example portable MFS device 100 with a surface 1402, and control buttons 1403 to 1406. Antenna 110 may be mounted under surface 1402. Control buttons 1403-1406 may allow a user to make adjustments to the stimulation parameters. FIG. 14D shows still another example portable MFS device 100 with antenna 110 and control buttons 1403-1406 for a user to make adjustments to the stimulation parameters.

Figure 15:
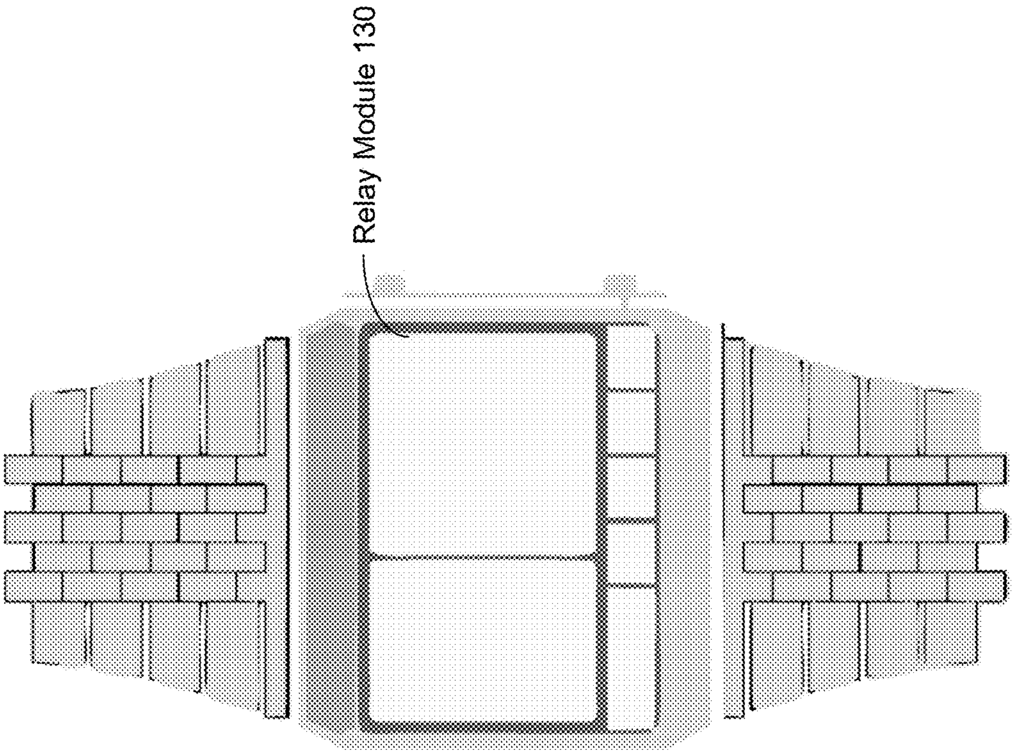
FIG. 15 depicts relay module in the configuration of a watch.

FIG. 15 depicts the MFS and Tx antenna in the configuration of a watch or other strap on arm unit. In certain embodiments, the Tx antenna is located on the perimeter of the watch face, or optionally on the strap of the watch or arm unit.

A number of implementations have been described. Nevertheless, it will be understood that various modifications may be made. Accordingly, other implementations are within the scope of the following claims.

What is claimed is:

1. A system comprising:

a wireless medical device configured to be implanted inside a patient and to be remotely powered by energy in radio frequency (RF) signals via electrical radiative coupling;

a relay device configured to direct RF signals to the wireless medical device; and a control device configured to:

generate a first RF signal for the wireless medical device; and direct the first RF signal to the relay device, wherein the wireless medical device is powered solely by energy in the first RF signal.

2. The system of claim 1, wherein the relay device includes at least one antenna and the first RF signal is transmitted via electrical radiative coupling and without inductive coupling to the relay device.

3. The system of claim 1, wherein the relay device is a layered structure that comprises:

a receive antenna layer, configured to receive the first RF signal transmitted by the control device;

at least one dielectric insulating layer; and a transmit antenna layer, separated from the receive antenna layer by the dielectric insulating layer, the transmit antenna layer configured to transmit a second RF signal based on the first RF signal to the wireless medical device to power the wireless medical device.

4. The system of claim 3, wherein the receive antenna layer includes one of a dipole antenna and a patch antenna, and the transmit antenna layer includes one of a dipole antenna and a patch antenna.

5. The system of claim 1, wherein the relay device comprises:

a receive antenna configured to receive the first RF signal transmitted by the control device; and a transmit antenna configured to transmit a second RF signal based on the first RF signal to the wireless medical device to power the wireless medical device.

6. The system of claim 5, wherein the first RF signal and the second RF signal have respective carrier frequencies that are within a range of about 800 MHz to about 6 GHz.

7. The system of claim 6, wherein the respective carrier frequencies of the first RF signal and the second RF signal are different.

8. The system of claim 1, wherein the relay device comprises a flexible circuit that includes a rectifier and an energy reservoir, wherein the rectifier converts the first RF signal to electrical energy that is stored in the energy reservoir.

9. The system of claim 1, wherein the relay device is configured to be implanted inside the patient.

10. The system of claim 1, wherein the relay device is configured to be placed exterior to the patient.

11. The system of claim 1, wherein the relay device is configured to be placed on skin of the patient.

12. The system of claim 1, wherein the relay device is configured to be placed on an item that is configured to be worn by the patient.

13. The system of claim 1, wherein the relay device is remotely powered by the energy in the first RF signal.

14. A method for facilitating neurophysiological treatment of a patient, the method comprising:

generating, at a control device outside of a patient, a radio frequency (RF) signal;

transmitting, from the control device, the RF signal to a relay device;

obtaining, at a wireless medical device implanted in the patient, energy via electrical radiative coupling based on the RF signal, the wireless medical device being powered solely by the energy in the RF signal;

generating, by the wireless medical device, a stimulation waveform using the energy; and applying, by the wireless medical device, the stimulation waveform to excitable tissue of the patient.

15. The method of claim 14, further comprising:

obtaining, at the relay device, the RF signal;

transmitting, by the relay device, a second RF signal based on the RF signal; and receiving, by the wireless medical device, the second RF signal, wherein the wireless medical device obtains energy from the second RF signal.

16. The method of claim 14, wherein the relay device is implanted in the patient.

17. The method of claim 14, further comprising:

transmitting, from the control device, a second RF signal to the relay device; and transmitting, from the relay device, a third RF signal to the wireless medical device, wherein the wireless medical device generates the stimulation waveform based on the third RF signal.

18. The method of claim 17, wherein the second RF signal carries the stimulation waveform.

19. The method of claim 17, further comprising configuring polarity of at least one electrode of the wireless medical device based on the third RF signal that encodes polarity setting information of the at least one electrode.

20. The method of claim 14, further comprising:

obtaining, at the relay device, the RF signal; and obtaining, at the relay device, second energy via electrical radiative coupling based on the RF signal, the relay device being powered by the second energy such that the relay device does not require electrical power from another source other than the RF signal to operate.

* * * * *